US012708340B2

(12) United States Patent
Vancamberg et al.

(10) Patent No.: US 12,708,340 B2
(45) Date of Patent: Aug. 18, 2026

(54) SMART DIGITAL BREAST TOMOGRAPHY IMAGE ACQUISITION SYSTEM AND METHOD

(71) Applicant: GE Precision Healthcare LLC, Waukesha, WI (US)

(72) Inventors: Laurence Vancamberg, Poissy (FR); Razvan Iordache, Clamart (FR); Clément Jailin, Antony (FR)

(73) Assignee: GE Precision Healthcare LLC, Waukesha, WI (US)

( * ) Notice: Subject to any disclaimer, the term of this patent is extended or adjusted under 35 U.S.C. 154(b) by 240 days.

(21) Appl. No.: 18/747,649

(22) Filed: Jun. 19, 2024

(65) Prior Publication Data

US 2025/0387093 A1 Dec. 25, 2025

(51) Int. Cl.
*A61B 6/00* (2024.01)
*A61B 6/02* (2006.01)
(Continued)

(52) U.S. Cl.
CPC .............. *A61B 6/545* (2013.01); *A61B 6/025* (2013.01); *A61B 6/0414* (2013.01); *A61B 6/466* (2013.01);
(Continued)

(58) Field of Classification Search
CPC ....... A61B 6/025; A61B 6/0414; A61B 6/466; A61B 6/467; A61B 6/482; A61B 6/488;
(Continued)

(56) References Cited

U.S. PATENT DOCUMENTS 7,577,282 B2 8/2009 Gkanatsios et al.
7,929,743 B2 4/2011 Khorasani
(Continued)

FOREIGN PATENT DOCUMENTS

EP 3964132 B1 7/2023
WO 2012107057 A1 8/2012

OTHER PUBLICATIONS

Erdal Pekel et al., Runtime optimization of acquisition trajectories for x-ray computed tomography with a robotic sampleholder, Engineering Research Express, 2023, 15 pages.

*Primary Examiner* — Dani Fox
(74) *Attorney, Agent, or Firm* — Boyle Fredrickson, S.C.

(57) ABSTRACT

According to an exemplary embodiment of the disclosure, an imaging system and method is provided for determining the need for generation of enhanced diagnostic images of a patient. The imaging system includes a radiation source operable at to emit radiation at multiple energy levels, a detector alignable with the radiation source, a controller operably connected to the radiation source and the detector to generate image data in an imaging procedure, and a computer aided detection (CAD) system configured to analyze initial projection images to locate any regions of interest (ROI) within the object. Upon locating analyzing one or more ROIs within the initial projection images, the system and method can determine imaging parameters to acquire one or more additional projection images of the object, and can process the one or more initial projection images and the one or more additional projection images to form one or more enhanced diagnostic images.

21 Claims, 9 Drawing Sheets

(51) Int. Cl.
*A61B 6/04* (2006.01)
*A61B 6/46* (2024.01)
*A61B 6/50* (2024.01)

(52) U.S. Cl.
CPC .............. *A61B 6/467* (2013.01); *A61B 6/502* (2013.01); *A61B 6/5205* (2013.01); *A61B 6/5235* (2013.01); *A61B 6/5258* (2013.01)

(58) Field of Classification Search
CPC ..... A61B 6/502; A61B 6/5205; A61B 6/5235; A61B 6/5258; A61B 6/545
See application file for complete search history.

(56) References Cited

U.S. PATENT DOCUMENTS

| | | | |
|---|---|---|---|
| 11,246,551 B2 | 2/2022 | Butani et al. | |
| 2016/0183899 A1 | 6/2016 | Vancamberg et al. | |
| 2018/0130201 A1* | 5/2018 | Bernard | A61B 6/025 |
| 2020/0146645 A1* | 5/2020 | Nakayama | A61B 6/482 |
| 2021/0259649 A1* | 8/2021 | Milioni De Carvalho | G06T 7/337 |
| 2024/0074718 A1 | 3/2024 | Jailin et al. | |

* cited by examiner

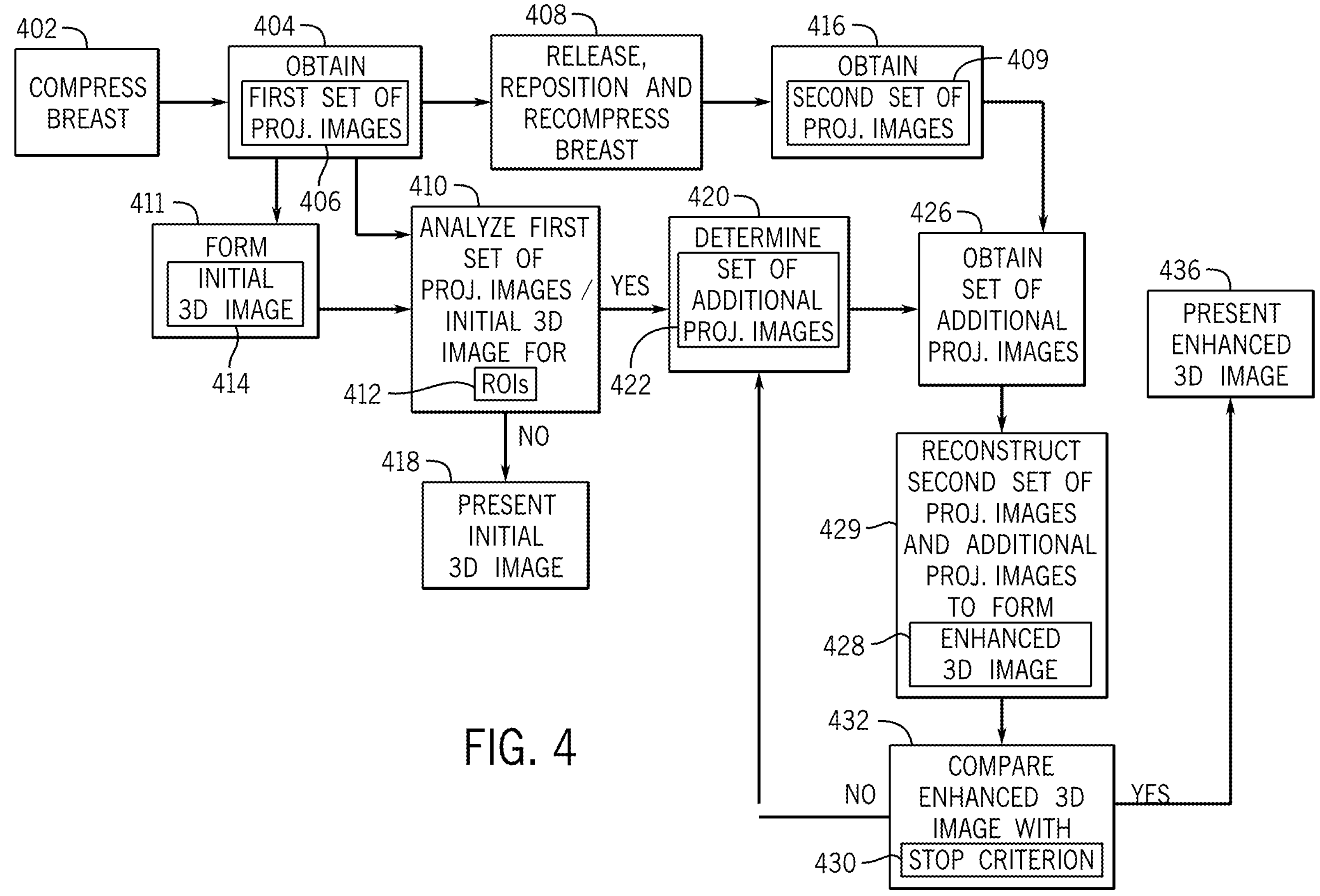
402
COMPRESS BREAST
404
OBTAIN
FIRST SET OF PROJ. IMAGES
406
408
RELEASE, REPOSITION AND RECOMPRESS BREAST
416
OBTAIN
SECOND SET OF PROJ. IMAGES
409
411
FORM
INITIAL 3D IMAGE
414
410
ANALYZE FIRST SET OF PROJ. IMAGES / INITIAL 3D IMAGE FOR
ROIs
412
YES
420
DETERMINE
SET OF ADDITIONAL PROJ. IMAGES
422
426
OBTAIN SET OF ADDITIONAL PROJ. IMAGES
436
PRESENT ENHANCED 3D IMAGE
NO
418
PRESENT INITIAL 3D IMAGE
429
RECONSTRUCT SECOND SET OF PROJ. IMAGES AND ADDITIONAL PROJ. IMAGES TO FORM
428
ENHANCED 3D IMAGE
432
COMPARE ENHANCED 3D IMAGE WITH
430
STOP CRITERION
NO
YES
FIG. 4

SMART DIGITAL BREAST TOMOGRAPHY IMAGE ACQUISITION SYSTEM AND METHOD

FIELD OF THE DISCLOSURE

The present disclosure relates generally to medical imaging systems, including mammography systems and devices, and more specifically to system and methods for determining whether additional images of the patient are required for diagnostic purposes.

BACKGROUND OF THE DISCLOSURE

Embodiments of the invention relate generally to X-ray medical imaging, and more particularly to devices, systems and methods employed to perform various imaging procedures, such as mammography imaging procedures including but not limited to spectral mammography (SM), such as 2D/3D dual-energy contrast-enhanced (CE) mammography exams, full-field digital mammography (FFDM) or digital breast tomosynthesis (DBT) mammography exams.

Spectral mammography (SM) is an X-ray imaging modality used to scan breasts for screening, diagnosis and/or interventional examinations that uses either multiple x-ray acquisition at different energy giving multiple images, or one x-ray acquisition with an energy discriminant detector that will be used to create multiple images. The effectiveness of spectral mammography is affected by numerous factors, one of which is the two-dimensional (2D) rendering of images obtained using SM.

Alternative systems to SM are also known for breast imaging. Some examples include full-field digital mammography (FFDM), which captures the image directly onto a flat-panel detector, computed radiography, which involves the use of a cassette that contains an imaging plate, or digital breast tomosynthesis (DBT). A digital breast tomosynthesis (DBT) or mammography-tomography (mammo-tomo) system is a dedicated mammography system that acquires several (e.g., tens of) angularly offset projection X-ray images and uses the resulting X-ray image data to reconstruct three-dimensional (3D) image datasets.

The 3D image datasets are used to form various volumetric representations of the imaged breast, including an entire 3D volume of the breast, and various 3D sections of the 3D volume, such as slices or slabs constituting specified thicknesses of the 3D volume oriented to provide the desired view of one or more regions of interest (ROI) detected within the 3D image dataset.

In addition, when the 3D image datasets of the breast have been produced, after being utilized in a suitable diagnosis procedure, they can be utilized to guide a biopsy device employed with the DBT system into the breast to obtain a biopsy of any one or more regions of interest (ROI) identified within the 3D image datasets. In DBT systems, the biopsy device is disposed directly on the DBT system in order to be able to perform the biopsy utilizing the 3D image dataset to guide the biopsy device to the ROI.

With regard to the use of mammography devices, the process of obtaining high quality mammographic images from breast tissue requires a technician to position the breast of a patient between one or more paddles that compress the breast in order to immobilize and flatten it during image acquisition. The compression force applied to a breast improves image quality by reducing the thickness of the breast while spreading the breast tissue over a larger area; this facilitates interpretation of obtained imagery since the amount of overlying tissue for structures within the imaged breast is minimized. Reduction of the breast thickness by compression is also important in managing patient radiation dosage. In general, the thicker the compressed breast, the more x-ray attenuation.

In some mammography spectral procedures, the images or projections of the breast under compression on the imaging device can be obtained using a low energy (LE) acquisition (tube voltage of the X-ray emitter of between about 20-40 kVp) and a high energy (HE) acquisition (tube voltage of the X-ray emitter of between about 45-80 kVp). The tissues of the breast have different attenuations of the LE and HE X-rays produced by the X-ray emitter, such that different tissues are represented more distinctly in the LE image data versus the HE image data, and vice versa. This is particularly true in the case of contrast enhanced (CE) imaging procedures, such as CE spectral mammography (CESM) and contrast enhanced digital breast tomosynthesis (CE-DBT). If utilized in these procedures, the contrast agent, e.g., iodine, injected into the patient prior to the performance of the LE and HE imaging procedures can enhance the attenuation of numerous types of breast tissues constituting ROIs, including masses, and cancerous tumors, among others, such that the ROIs are more clearly illustrated in the image data, and particularly within recombined images formed from the image data provided by the LE and HE acquisitions, whether contrast enhanced or not, in any of a number of known manners in order to produce high quality combined 2D and/or 3D images of the breast for diagnostic purposes.

The image data provided by the LE and HE acquisitions, whether contrast enhanced or not, can subsequently be combined in any of a number of known manners in order to produce high quality combined 2D and/or 3D images of the breast for diagnostic purposes.

With prior art mammography imaging devices and the procedures performed thereby, the angular spacing or trajectories of the x-ray tube for the projection image acquisitions are fixed for a mammography imaging procedure in order to provide single or dual energy images employed to form the combined image or volume.

However, as a result of performing the projection image acquisitions at only the predetermined x-ray tube trajectories in the mammography imaging procedure, there is the potential for the combined image and/or volume to not include enough information for diagnostic purposes. In those situations, it is necessary for the patient to come back for a subsequent imaging procedure, such as a magnified or spot view imaging procedure, or imaging procedure employing an different imaging modality, to provide the necessary diagnostic image data.

Therefore, it is desirable to develop a mammography imaging system and method that can selectively conduct additional projection image acquisitions in situations where the additional projection image acquisitions are necessary to provide a diagnostic enhancement to the images produced by the initial projection image acquisitions performed by the mammography imaging system for clinical review.

SUMMARY OF THE DISCLOSURE

According to an aspect of an exemplary embodiment of the present disclosure, a mammography system includes a radiation source operable at to emit radiation at multiple energy levels, a detector alignable with the radiation source, the detector having a surface on which an object to be imaged is adapted to be positioned, and a controller operably connected to the radiation source and the detector to control the operation of the radiation source and detector to generate image data in an imaging procedure performed by the imaging system, the controller including a central processing unit and interconnected database for processing the image data from the detector to create images, a display operably connected to the controller for presenting information to a user, and a user interface operably connected to the controller to enable user input to the controller, wherein the controller is configured to acquire one or more initial projection images of the object each acquired along a pre-defined trajectory, to reconstruct an initial 3D image of the object from the one or more initial images, to analyze the initial 3D images and/or initial projection images to locate one or more triggering attributes, characteristics or findings within the object, determine one or more imaging parameters for a set of one or more additional projection images of the object, the set of additional projection images to be acquired at one or more trajectories of the x-ray tube other than employed for acquiring the one or more initial projection images if one or more triggering attributes, characteristics or findings are located in the object, to acquire the set of additional projection images, to process the initial 3D image and the set of additional projection images to form an enhanced 3D image, and to comparing the enhanced 3D image to a stop criterion.

According to still another aspect of an exemplary embodiment of the present disclosure, a method for determining the need for generation of enhanced diagnostic images of a object includes the steps of providing an imaging system having a radiation source operable at to emit radiation at multiple energy levels, a detector alignable with the radiation source, the detector having a surface on which an object to be imaged is adapted to be positioned and a controller operably connected to the radiation source and the detector to control the operation of the radiation source and detector to generate image data in an imaging procedure performed by the imaging system, the controller including a central processing unit and interconnected database for processing the image data from the detector to create images, a display operably connected to the controller for presenting information to a user, and a user interface operably connected to the controller to enable user input to the controller, positioning the object on the surface between the radiation source and the detector, acquiring one or more initial projection images of the object along a pre-defined trajectory for each initial projection image, reconstructing an initial 3D image of the object from the one or more initial projection images, analyzing the initial 3D images and/or initial projection images to locate one or more triggering attributes, characteristics or findings within the object, determining one or more imaging parameters for a set of one or more additional projection images of the object, the set of additional projection images to be acquired at one or more trajectories different than employed for acquiring the one or more initial projection images if one or more triggering attributes, characteristics or findings are located in the object, acquiring the set of additional projection images, processing the initial 3D image and the set of additional projection images to form an enhanced 3D image, and comparing the enhanced 3D image to a stop criterion.

These and other exemplary aspects, features and advantages of the invention will be made apparent from the following detailed description taken together with the drawing figures.

BRIEF DESCRIPTION OF THE DRAWINGS

The drawings illustrate the best mode currently contemplated of practicing the present invention.

In the drawings:

FIG. 4 is a flowchart illustrating the operation of the mammography system in accordance with a second embodiment of the disclosure.

DETAILED DESCRIPTION OF THE DRAWINGS

Figure 1:
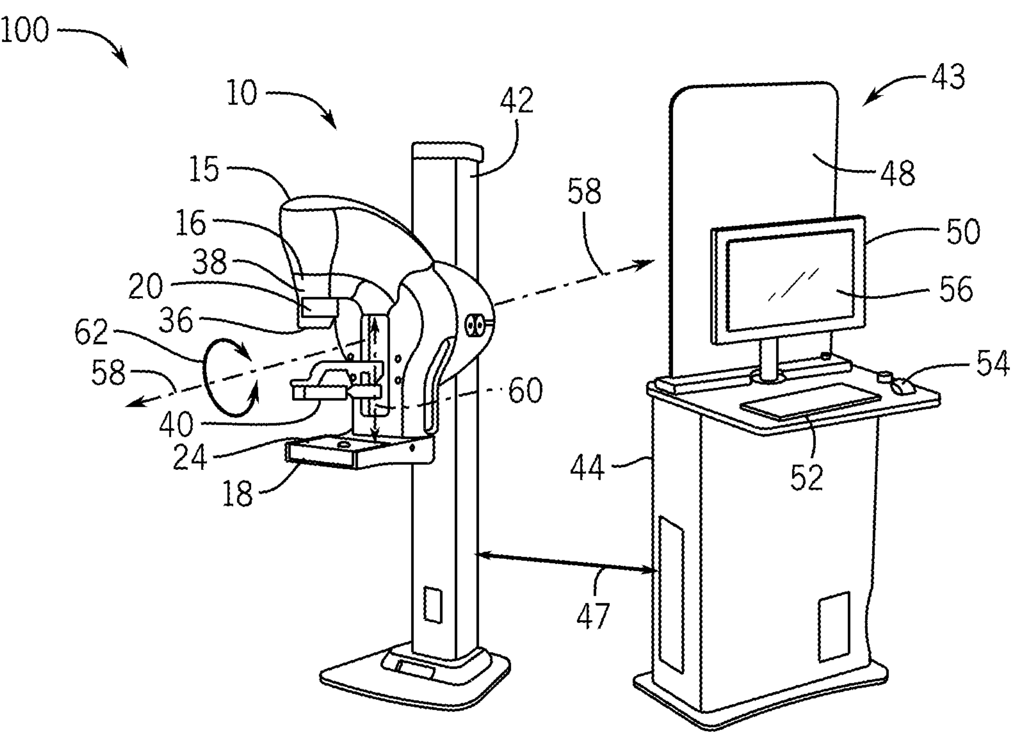
FIG. 1 is an isometric view of an imaging system in the form of a mammography system for imaging the breast tissue of a patient, in accordance with an embodiment of the disclosure.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

As used herein, "electrically coupled", "electrically connected", and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present.

Further, while the embodiments disclosed herein are described with respect to a digital mammography apparatus for both 2-dimensional (2D) and 3-dimensional (3D) imaging of breast tissue including spectral mammography (single or multi-energy), it is to be understood that embodiments of the invention may be applicable to other types of imaging devices for either or both 2D and 3D imaging including, for example, fluoroscopy, full-field digital mammography (FFDM), and digital breast tomosynthesis (DBT), as well as for imaging procedures for tissues other than breast tissue. Further still, embodiments of the invention may be used to analyze tissue, generally, and are not limited to analyzing human tissue.

During imaging procedures using a digital mammography system, the breast of a patient is compressed and an x-ray source may be rotated around the breast within a range of angles in positive and negative directions from a medial position. Certain imaging procedures, including digital breast tomosynthesis (DBT) performed with a digital mammography system, acquire multiple projection images (2D) of the breast at various positions of the x-ray tube at one or more x-ray energy levels, e.g., low energy (LE) or high energy (HE). Other imaging procedures, including contrast enhanced digital breast tomosynthesis (CE-DBT) performed with a digital mammography system, acquire multiple projection images (2D) of the breast at various positions of the x-ray tube with different x-ray energy levels, e.g., both LE and HE, to form a dual energy image of the breast. A dual energy image may be generated from two images, where the two images include a first image acquired with low radiation energy (termed a low energy image, or LE) and a second image acquired with high radiation energy (termed a high energy image, or HE). A digital subtraction process may be used to generate the dual energy (DE) image from the LE image and the HE image, such that background features are removed from the DE image and the contrast-enhanced features (e.g., the lesion) are more clearly visualized. In certain dual energy imaging procedures, including contrast-enhanced digital breast tomosynthesis (CE-DBT), the visualization of one or more regions of interest (ROIs) in the dual energy image can be enhanced by the administration of a contrast agent, such as iodine, to an imaging subject (e.g., patient).

Referring to FIG. 1, a digital mammography system 100, such as that disclosed in US Patent Application Publication No. US2024/0074718, entitled *Methods and Systems For Digital Mammography Imaging*, the entirety of which is expressly incorporated by reference herein for all purposes, is shown including an x-ray system 10 for performing a mammography procedure, according to an embodiment of the disclosure.

The x-ray system 10 includes a support structure 42, to which a radiation source 16, a radiation detector 18, and a collimator 20 are attached. The radiation source 16 is housed within a gantry 15 that is movably coupled to the support structure 42. In particular, the gantry 15 may be mounted to the support structure 42 such that the gantry 15 including the radiation source 16 can rotate around an axis 58 in relation to the radiation detector 18. An angular range of rotation of the gantry 15 housing the radiation source 16 indicates a rotation up to a desired degree in either direction about the axis 58, as indicated by arrow 62. For example, the angular range of rotation of the radiation source 16 may be $-\theta$ to $+\theta$, where $\theta$ may be such that the angular range is a limited angle range, less than 360 degrees. An exemplary x-ray system may have an angular range of ±11 degrees, which may allow rotation of the gantry (that is rotation of the radiation source) from −11 degrees to +11 degrees about an axis of rotation of the gantry. The angular range may vary depending on the manufacturing specifications. The angular range for digital mammography systems may be approximately ±11 degrees to ±60 degrees, depending on the manufacturing specifications.

The radiation source 16 is directed toward a volume or object to be imaged and is configured to emit radiation rays at desired times to acquire one or more images. The radiation detector 18 is configured to receive the radiation rays via a surface 24. The detector 18 may be any one of a variety of different detectors, such as an x-ray detector, digital radiography detector, or flat panel detector. The collimator 20 is disposed adjacent to the radiation source 16 and is configured to adjust an irradiated zone of a subject.

In some embodiments, the system 10 may further include a patient shield 36 mounted to the radiation source 16 via face shield rails 38 such that a patient's body part (e.g., head) is not directly under the radiation. The system 10 may further include a compression paddle 40, which may be movable upward and downward in relation to the support structure along a vertical axis 60. Thus, the compression paddle 40 may be adjusted to be positioned closer to the radiation detector 18 by moving the compression paddle 40 downward toward the detector 18, and a distance between the detector 18 and the compression paddle 40 may be increased by moving the compression paddle upward along the vertical axis 60 away from the detector. The movement of the compression paddle 40 may be adjusted by a user via compression paddle actuator (not shown) included in the x-ray system 10. The compression paddle 40 may hold a body part, such as a breast, in place against the surface 24 of the radiation detector 18. The compression paddle 40 may compress the body part and hold the body part still in place while optionally providing apertures to allow for insertion of a biopsy needle, such as a core needle or a vacuum assisted core needle. In this way, compression paddle 40 may be utilized to compress the body part to minimize the thickness traversed by the x-rays and to help reduce movement of the body part due to the patient moving. The x-ray system 10 may also include an object support (not shown) on which the body part may be positioned.

The digital mammography system 100 may further include a workstation 43 comprising a controller 44 including at least one processor and a memory. The controller 44 may be communicatively coupled to one or more components of the x-ray system 10 including one or more of the radiation source 16, radiation detector 18, the compression paddle 40, and a biopsy device. In an embodiment, the communication between the controller and the x-ray system 10 may be via a wireless communication system. In other embodiments, the controller 44 may be in electrical communication with the one or more components of the x-ray system via a cable 47. Further, in an exemplary embodiment, as shown in FIG. 1, the controller 44 is integrated into the workstation 43. In other embodiments, the controller 44 may be integrated into one or more of the various components of the system 10 disclosed above. Further, the controller 44 may include processing circuitry and associated electronic memory devices that execute stored program logic and may be any one of different computers, processors, controllers, or combination thereof that are available for and compatible with the various types of equipment and devices used in the x-ray system 10.

The workstation 43 may include a radiation shield 48 that protects an operator of the system 10 from the radiation rays emitted by the radiation source 16. The workstation 43 may further include a user interface 50, formed of one or more of a keyboard 52, mouse 54, and/or other appropriate user input devices that facilitate control of the system 10 via a user interface 50, as well as an interconnected display 56, which can also function as the user interface 50.

The controller 44 may adjust the operation and function of the x-ray system 10. As an example, the controller 44 may provide timing control, as to when the x-ray source 16 emits x-rays, and may further adjust how the detector 18 reads and conveys information or signals after the x-rays hit the detector 18, and how the x-ray source 16 and the detector 18 move relative to one another and relative to the body part being imaged. The controller 44 may also control how information, including images 45 presented on display 50 and data acquired during the operation, is processed, displayed, stored, and manipulated. Various steps of the method of operation of the x-ray system 10 and processing of the image data obtained thereby as described herein with respect to FIGS. 3-8 performed by the controller 44, may be provided by a set of instructions stored in non-transitory memory of the controller 44.

Further, as stated above, the radiation detector 18 receives the radiation rays 22 emitted by the radiation source 16. In particular, during imaging with the x-ray system, a projection image of the imaging body part may be obtained at the detector 18. In some embodiments, data, such as projection image data, received by the radiation detector 18 may be electrically and/or wirelessly communicated to the controller 44 from the radiation detector 18. The controller 44 may then reconstruct one or more scan images based on the projection image data, by implementing a reconstruction algorithm, for example. The reconstructed image may be displayed to the user on the user interface 50 via a display screen 56.

The radiation source 16, along with the radiation detector 18, forms part of the x-ray system 10 which provides x-ray imagery for the purpose of one or more of screening for abnormalities, diagnosis, dynamic imaging, and image-guided biopsy. For example, the x-ray system 10 may be operated in a mammography mode for screening for abnormalities. During mammography, a patient's breast is positioned and compressed between the detector 18 and the compression paddle 40. Thus, a volume of the x-ray system 10 between the compression paddle 40 and the detector 18 is an imaging volume. The radiation source 16 then emits radiation rays on to the compressed breast, and a projection image of the breast is formed on the detector 18. The projection image may then be reconstructed by the controller 44, and displayed on the interface 50. During mammography, the gantry 15 may be adjusted at different angles to obtain images at different orientations, such as a cranio-caudal (CC) image and a medio-lateral oblique (MLO) image. In one example, the gantry 15 may be rotated about the axis 58 while the compression paddle 40 and the detector 18 remain stationary. In other examples, the gantry 15, the compression paddle 40, and the detector 18 may be rotated as a single unit about the axis 58.

Further, the x-ray system 10 may be operated in a tomosynthesis mode for performing digital breast tomosynthesis (DBT). During tomosynthesis, the x-ray system 10 may be operated to direct low-dose radiation towards the imaging volume (between the compression paddle 40 and the detector 18) at various angles over the angular range of the x-ray system 10. Specifically, during tomosynthesis, similar to mammography, the breast is compressed between the compression paddle 40 and the detector 18. The radiation source 16 is then rotated from $-\theta$ to $+\theta$, and a plurality of projection images of the compressed breast is obtained at regular angular intervals over the angular range. For example, if the angular range of the x-ray system is ±11 degrees, 22 projection images may be captured by the detector during an angular sweep of the gantry at approximately one every one degree, generating a set of angulated x-ray images. The plurality of projection images are then processed by the controller 44 to generate a plurality of DBT image slices. The processing may include applying one or more reconstruction algorithms to reconstruct three dimensional image of the breast. Furthermore, the x-ray system may be configured to perform a DBT-guided biopsy procedure. Accordingly, in some exemplary embodiments, the system 10 may further include a biopsy device comprising a biopsy needle for extracting a tissue sample for further analysis.

In some examples of dual energy DBT imaging procedures, or dual energy stereotactic procedures, low-energy (LE) and high-energy (HE) projection image acquisitions are performed of the breast or other tissue with at least two different positions of the x-ray source with respect to the detector. The projection images are then recombined to display material-specific information with regard to the internal structure of the tissue being imaged.

The use of contrast agents can be coupled with images taken using dual-energy imaging processes and technology. The contrast agents are taken up in the blood vessels surrounding a cancerous lesion in the breast and/or ROI, thereby providing a contrasting image for a period of time with respect to the surrounding tissue, enhancing the ability to locate the lesion.

In particular, full field digital mammography (FFDM) (2D) and digital breast tomosynthesis (DBT) (3D) imaging modalities one or more projection images of the breast are acquired at various angular positions of the x-ray tube. For each view (single view in FFDM, multiple views for DBT), a projection image is acquired which in DBT, are each used to reconstruct a 3D volume. Image reconstruction may be performed based on simulations of the x-ray image chain, via calibrations on a reference phantom, or any other suitable 3D-reconstruction process. Additionally, in the continuous mode of acquisition where the x-ray tube moves continuously the projection images are used to reconstruct an initial 3D image or 3D volume that is reviewed for diagnostic purposes.

In CE-DBT, non-paired HE and LE images may be acquired for each view and an HE volume, LE volume, and recombined volumes may be reconstructed for the ROI. For example, the HE and LE views may be interleaved during the DBT scan (alternatively HE, LE, HE, LE, HE, LE, etc.) with a switch from HE to LE then to HE again etc., for each angulated position of the x-ray tube. In embodiment where a contrast agent is employed, the LE and HE images are usually obtained at mean energies above and below the k-edge of the contrast agent. At x-ray energies just above the k-edge of the contrast agent, the absorption of x-rays is increased resulting in an increase of contrast from the iodine contrast agent in the HE image.

Figure 2:
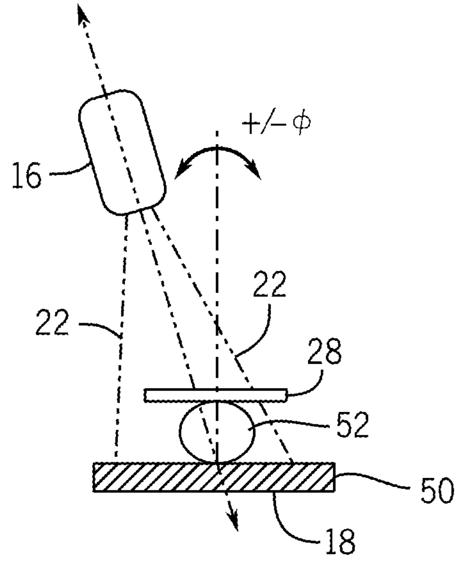
FIG. 2 is a diagram of the mammography device of FIG. 1, showing the radiation source of the mammography system in a scanning position, in accordance with an embodiment of the disclosure.

Referring now to FIG. 2, in operation of the x-ray system 10 in accordance with an embodiment, the breast 64 of the patient may be placed onto the surface 24 of the radiation detector 18. The compression paddle 40, under control of the controller 44, moves towards the detector 18 to compress the breast 64 against the surface 24 of the detector 18 such that the breast 64 is immobilized. Movement of the compression paddle 40 towards the detector 18 to compress the breast 64 against the support plate/detector 18 defines a compression phase of the x-ray system 10. Once a target compression is achieved, movement of the compression paddle 40 is halted and the compression paddle 40 and the detector 18 are held in fixed position to clamp the breast 64 therebetween (referred to herein as the clamping phase) so that the imaging or other procedures, e.g., a biopsy, may be commenced. During an imaging procedure, the radiation source 16 is selectively adjusted such that it is moved/rotated to a first scanning position and scans the breast 64. The radiation detector 18 receives the radiation rays 22 passing through the breast 64 and sends data to the controller 44 which then generates one or more x-ray images of the breast 64.

Figure 3:
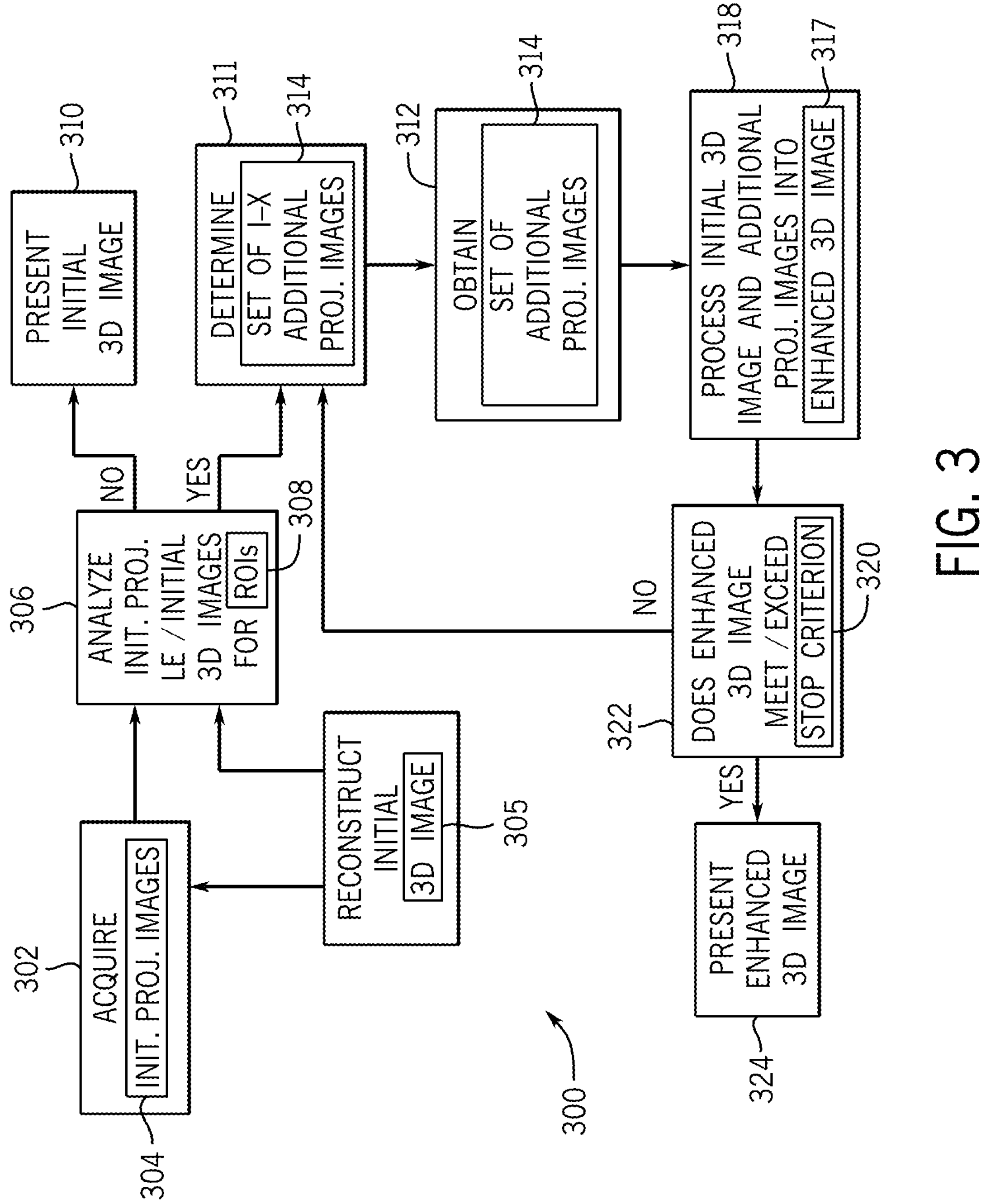
FIG. 3 is a flowchart illustrating the operation of the mammography system in accordance with a first embodiment of the disclosure.

Looking now at FIG. 3, a first exemplary embodiment of a method 300 of operation of the x-ray system 10/mammography system 100 in accordance with the present disclosure is illustrated. The method 300 is performed using the x-ray system 10/mammography system 100 in a DBT imaging procedure to selectively determine from the initial projection images acquired by the x-ray system 10/mammography system 100 whether the acquisition of one or more additional projection images is required to provide enhanced images processed from the initial projection images and additional projection images with clinical diagnostic information for review. In various embodiments, additional projection images are acquired at other angular positions or trajectories for the x-ray source than those at which the initial projection images were obtained using the x-ray system 10/mammography system 100.

In the method 300, after compression of the breast on the x-ray system 10 between the detector 18 and the compression paddle 40, in step 302 a number of initial projection images 304, such as from 1 to N or 1–N initial projection images 304, are obtained of the breast 64 at various angular positions of the radiation source 16 relative to the compressed breast 64 and the radiation detector 18, optionally in conjunction with the administration of a contrast agent to the patient/breast 64. In one exemplary embodiment, the initial projection images 304 can be LE images or HE images. In an exemplary embodiment, the initial projection images 304 can be 3D images formed or reconstructed from image data obtained as a part of a DBT (3D) screening imaging procedure. In step 306, the initial projection images 304, and/or an initial 3D image or volume 305 that is reconstructed from the initial projection images 304, is analyzed by a user of the x-ray system 10, such as when presented to the user on the display 56, or by the controller 44, such as through the use of a computer aided diagnosis (CAD) program contained within and/or as part of the controller 44 to determine the presence and/or type of any one or more attributes, characteristics, risk factors, densities or findings, such as a BI-RADS score for portions of or the entire breast, suspicious areas or regions of interest (ROIs), hereinafter generally described as ROIs 308, identified within the initial projection images 304/initial 3D image 305 and employed as the trigger for manually and/or automatically performing subsequent acquisition(s) to obtain additional projection images of the object/breast 64. The analysis provided by the CAD/controller 44 can be performed in real time to provide the results of the analysis to the user as feedback during the screening imaging procedure. If no ROIs 308 are determined to be present in the initial projection images 304/initial 3D image 305, the method 300 proceeds to step 310 to present the finding of no ROIs 308 within the initial projection images 304/initial 3D image 305, optionally along with the initial projection images 304/initial 3D image 305, and terminates the screening imaging procedure.

Alternatively, should the user or controller 44 determine a ROI 308 is present in the initial projection images 304/initial 3D image 305, in step 311 the controller 44 utilizes information from the initial projection images 304/initial 3D image 305 on the location and/or type of ROI(s) 308 present within the breast 64 to determine imaging parameters for acquiring a set of additional projection images 314 to be performed by the x-ray system 10 in order to obtain further diagnostic information concerning the ROI(s) 308. The determination of the imaging parameters for the set of additional projection images 314 includes selecting the at least one or more of the number, angular position, angular spacing/or energy level, which can be the same or different than the energy level used for the initial projection images 304 or can be dual energy levels, of each of the individual acquisitions to be obtained within the set of additional projection images 314. In one embodiment, the step 311 can be performed by the user of the x-ray system 10 through the user interface 50. In an alternative embodiment, in step 311 the controller 44 can include processing circuitry and associated electronic memory devices that execute stored program logic in the form of an artificial intelligence that operates to determine optimized imaging parameters/the set of additional projection images 314 for enhancing the diagnostic information on the detected ROI(s) 308 in an adaptive or case or procedure-specific manner. Further, in still another alternative embodiment of step 311, the imaging parameters/set of additional projection images 314 are selected in a predefined manner using the information determined on the ROI(s) 308, such as the tissues type(s) forming the ROI(s) 308 and the location of the ROI(s) 308, among others, with the set of additional projection images 314 having preset numbers, angular position, angular spacing, and energy level of the individual acquisitions to be obtained within the set of additional projection images 314.

Regardless of the manner in which the determination of the imaging parameters for the set of additional projection images 314 is performed in step 311, once the parameters for determination of the set of additional projection images 314 are determined, in step 312 the x-ray system 10 is operated under the direction of the user to perform a subsequent DBT imaging procedure or acquisition to obtain the set of additional projection images 314 with the breast 64 at the same compression as in step 302. In one exemplary embodiment of step 312, the set of additional projection images 314 includes a number of, e.g., 1 to X, additional projection images that are acquired at other x-ray tube positions. These tube positions for the set of additional projection images 314 can be based on the type and/or shape of ROI(s) 308 located, e.g., a larger angulation range or angle (e.g. between each additional projection image to be obtained) for masses, or at a smaller angulation range or angle (e.g. between each additional projection image to be obtained) for microcalcifications, or based on the ROI(s) 308 being outside of the plane of the prior x-ray tube position for the initial projection images 304, or based on computed ideal view(s) for the ROI(s) 308.

In the embodiment of FIG. 3, the set of additional projection images 314 are obtained in step 312 with the breast 64 under the same compression as employed for the acquisition of the initial projection images 304 in step 302, such that the set of additional projection images 314/initial projection images 304 are acquired with the breast 64 in the same position. Further, in step 312 the imaging parameters for the set of additional projection images 314 can be presented to the user, such as on the user interface 50, in order to show the user the number and type of images and x-ray tube positions forming the set of additional projection images 314 that are to be obtained, optionally along with information regarding the number and type of ROI(s) 308 necessitating the set of additional projection images 314.

After acquisition of the additional projection images 314, in step 318 the controller 44 processes each of the 1 to N initial projection images 304, and/or the initial 3D image 305, along with each of the N+1 to N+X additional projection images 314 to form or reconstruct one or more enhanced images, e.g., an enhanced 3D image 317 clearly presenting the location and other characteristics of the ROI(s) 308 within the enhanced 3D image 317 for diagnostic review by the user and/or reviewing physician. The reconstruction in step 318 can be performed by a suitable algorithm and/or processor executable instructions stored within the memory of the controller 44 or a remote memory accessible by the controller 44, where an example of a suitable reconstruction algorithm is provided in Rodriguez-Ruiz A, Teuwen J, Vreemann S, Bouwman R W, van Engen R E, Karssemeijer N, Mann R M, Gubern-Merida A, Sechopoulos I. *New Reconstruction Algorithm For Digital Breast Tomosynthesis: Better Image Quality For Humans And Computers. Acta radiologica* (Stockholm, Sweden: 1987) vol. 59, 9 (2018): 1051-1059. doi:10.1177/0284185117748487, the entirety of which is expressly incorporated herein by reference for all purposes.

In subsequent step 320, the enhanced 3D image 317 is analyzed by the controller 44 to determine whether the enhanced 3D image 317 meets or exceeds a stop criterion 322 for the imaging procedure. In one exemplary embodiment for the stop criterion 322, where the set of additional projection images 314 are based off of a preset subset of acquisition numbers and trajectories for a specified type of ROI(s) 308, the stop criterion 322 can be the conclusion of step 312 to obtain the set of additional projection images 314. In an alternative exemplary embodiment, the stop criterion 322 can be one or more image quality parameters or metrics for the enhanced 3D image 317, including but not limited to a preset value for the signal to noise ratio for the enhanced 3D image 317. In still other alternative exemplary embodiments, and alternatively in addition to previous embodiments, the stop criterion 322 can be one or more confidence scores determined by the CAD system regarding the ROI(s) 308 in the enhanced 3D image 317, a confidence score determined by the controller 44 and/or CAD system based on breast imaging reporting and data system (BI-RADS) categories associated with the enhanced 3D image 317, as can also be employed for the determination of the presence of an ROI(s) 308, as discussed previously, and/or a confidence score determined by the controller 44 and/or CAD system based on BI-RADS descriptors (e.g., contour type, shape, size, etc.) associated with the enhanced 3D image 317. In still other alternative exemplary embodiments, the stop criterion 322 can based on monitoring for any evolution and/or change of any ROI(s) 308 or finding(s) within or characteristic(s) of the object. For example, if the determination of the measure of the characteristic (e.g. size of the ROI(s) 308) evolves or changes significantly as detected within the additional projection images 314 and/or the enhanced 3D image/volume 317, the stop criterion 322 is not reached and further additional images 314 are acquired. Alternatively, if there is no evolution or change of the measure or variation in the determined characteristic, then the stop criterion 322 is determined to be met. In one exemplary implementation of the evaluation of the characteristic of the object as the stop criterion 322, if the evaluation is performed during the acquisition of the set of additional images 314, the check of the stop criterion 322 is completed after the acquisition of each additional projection 314. Alternatively, the check of the stop criterion 322 can be performed on the enhanced 3D image/volume 317 formed by combining/recombining the initial projection images 304 and the set of additional projection images 314.

If in step 320, the enhanced 3D image 317 meets or exceeds the selected stop criterion/criteria 322, the method 300 proceeds to step 324 to present the enhanced 3D image 317 and visualization of the ROI(s) 308 therein for review by the user and/or physician and terminates the screening imaging procedure.

Alternatively, should the enhanced 3D image 317 not meet the required stop criterion 322 as determined in step 320, the method returns to step 311 where the controller 44 utilizes the information from the enhanced 3D image 317 on the location and/or type of ROI(s) 308 present to determine imaging parameters for a further set of additional projection images 314 to be acquired by the x-ray system 10 in order to obtain further diagnostic information concerning the ROI(s) 308. The further set of additional projection images 314 are obtained in step 312 and reconstructed along with the enhanced 3D image 317 to provide a further enhanced 3D image 317 for comparison with the stop criterion 322 in step 320. The method 300 can proceed in this iterative manner until the result in step 320 is that the enhanced 3D image 317 meets or exceeds the stop criterion 322, where the method 300 proceeds to step 324 to present the enhanced 3D image 317 and visualization of the ROI(s) 308 therein within the initial 3D image 305 for review by the user and/or physician and terminates the screening imaging procedure.

Looking now at FIG. 4, in a second exemplary embodiment of the disclosure, a method 400 is employed where the set of additional projection images of the breast 64 is obtained in a DBT imaging procedure at a compression different from the compression at which the initial projection images were obtained. More specifically, the method 400 involves the positioning of the breast 64 in step 402 between the compression paddle 40 and the detector 18 to acquire a first set of initial projection images 406 of the breast 64, which can be either cranial-caudal (CC) images or medio-lateral oblique (MLO) images of the breast 64. Once compressed, in step 404, the x-ray system 10 is operated in a DBT imaging procedure to obtain the first set of projection images 406 of the breast 64 at selected angular positions of the radiation source 16 relative to the radiation detector 18 and the breast 64. Subsequently, in step 408, the breast 64 is released, repositioned and recompressed in order to operate the x-ray system 10 in another DBT imaging procedure to obtain a second set of projection images 409 of the breast 64 in the other of the CC/MLO view from that of the first set of projection images 406. Concurrently with the decompression, repositioning and second compression of the breast 64 on the x-ray system 10 in step 408 for the subsequent acquisition, in step 411 the first set of projection images 406 is reconstructed into an initial 3D image 414 which, in step 410 is analyzed, optionally along with the first set of projection images 406, by the user and/or CAD/controller 44 to determine the presence of any ROI(s) 412 within the first set of projections 406 and/or the initial 3D image 414. Further, during and/or subsequent to the analysis of the first set of projections 406 and/or the initial 3D image 414, in step

416, the x-ray system 10 is operated to perform the subsequent acquisition of the second set of projection images 409 of the breast 64.

If no ROIs 412 are located in the first set or projection images 406 and/or the initial 3D image 414, the method 400 proceeds to step 418 to present the finding of no ROIs 412 within the initial 3D image 414, optionally along with the presentation of the initial 3D image 414, and terminates the imaging procedure. Alternatively, if one or more ROI(s) 412 are found in the first set or projection images 406 and/or the initial 3D image 414, in step 420 the controller 44 utilizes the information from the initial 3D image 414 regarding the location and/or type of ROI(s) 412 present in the manner described previously to determine imaging parameters for a set of additional projection images 422 to be obtained by the x-ray system 10 in a DBT imaging procedure in order to obtain further diagnostic information concerning the ROI(s) 412. The set of additional projection images 422 are obtained in step 426 at the same compression of the breast 64 employed for the second set of projection images 409. Thus, the set of additional projection images 422 are reconstructed with the second set of projection images 409 to provide an enhanced 3D image 428 in step 429 for comparison with the stop criterion 430 in step 432.

In step 434, if the enhanced 3D image 428 meets or exceeds the selected stop criterion/criteria 430, the method 400 proceeds to step 436 to present the enhanced 3D image 428 and visualization of the ROI(s) 412 therein for review by the user and/or physician and terminates the imaging procedure.

Alternatively, should the enhanced 3D image 428 not meet the required stop criterion 430 as determined in step 434, the method returns to step 420 where the controller 44 utilizes the information from the enhanced 3D image 428 on the location and/or type of ROI(s) 412 present to determine imaging parameters for a further set of additional projection images 422 to be obtained by the x-ray system 10 in order to obtain further diagnostic information concerning the ROI(s) 412, The further set of additional projection images 422 are obtained in step 420 and reconstructed along with the enhanced 3D image 428 to provide a further enhanced 3D image 428 for comparison with the stop criterion 430 in step 434. The method 400 can proceed in this iterative manner until the result in step 434 is that the enhanced 3D image 428 meets or exceeds the stop criterion 430, wherein the method 400 proceeds to step 436 to present the enhanced 3D image 428 and visualization of the ROI(s) 412 therein for review by the user and/or physician and terminates the imaging procedure.

In any of the prior or subsequently described embodiments of the present disclosure, in the particular step of the method 300,400 where the set of additional projection images are obtained, the x-ray system 10 can be operated to adjust the collimator 20, or other applicable radiation focusing mechanism or device on the x-ray system 10 to focus the rays 22 onto an area including the ROI(s) 308,412. In this manner, the image data obtained in the set of additional acquisitions/HE images includes enhanced resolution on the ROI(s) 308,412 represented within enhanced 3D image formed by the reconstruction of the initial 3D image with the one or more sets of additional projection images obtained to achieve the stop criteria for the enhanced 3D image to provide highly detailed information regarding the location and other characteristics of the ROI(s) 308,412 for diagnostic review by the user and/or reviewing physician.

Figure 5:
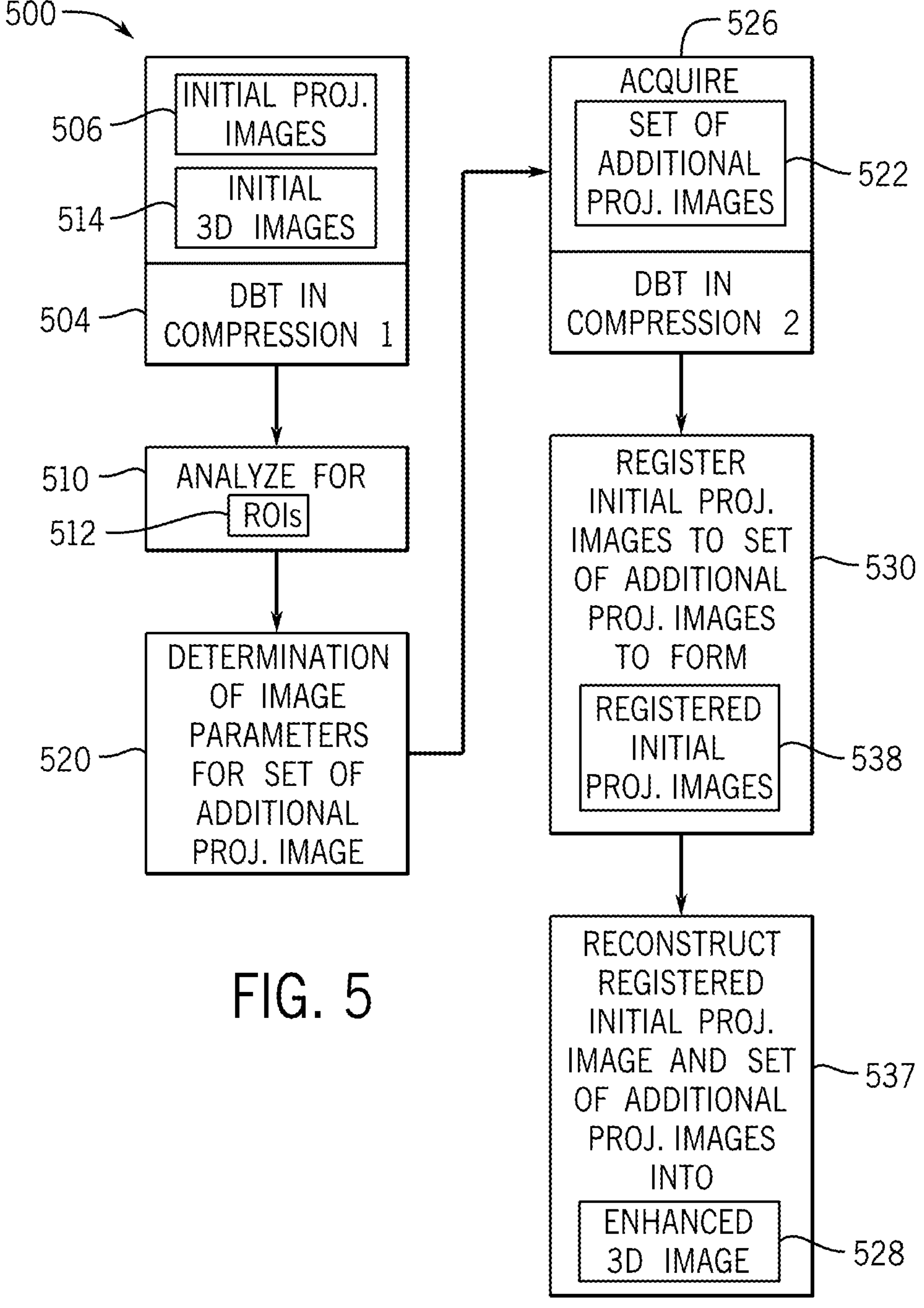
FIG. 5 is a flowchart illustrating the operation of the mammography system in accordance with a third embodiment of the disclosure.

Looking now at FIG. 5, and optionally in association with any other embodiment described herein, in a third exemplary embodiment of the disclosure, in certain embodiments the initial projection images 506 and/or initial 3D image 514 analyzed for the presence of the ROI(s) 512 and the set of additional projection image 522 that are combined to form the enhanced 3D image 528 for diagnostic review are obtained at different compressions of the breast 64. For example, in the method 500 the breast 64 is decompressed, repositioned and recompressed between the acquisition in step 504 of the initial projection images 506 and/or initial 3D image 514 that are initially analyzed in step 510 for the presence of ROIs(s) 512 and the determination of further acquisitions to be obtained in step 520, and the subsequent acquisition of the set of additional projection images 522 in step 526 for the same view, e.g., both the initial projection images 506 and the set of additional projection images 522 are each obtained at one of the CC or MLO views, but done at different compressions. In these situations, prior to the reconstruction in step 537 of the initial projection images 506 with the set of additional projection images 522 to provide the enhanced 3D image 528 for diagnostic review of ROIs 512 present in the breast, the initial projection images 506, or an initial 3D image 514 reconstructed therefrom, and the set of additional projection images 522, or an additional 3D image reconstructed therefrom, must be registered to one another in step 530 to form registered initial projection images 538 or a registered initial 3D image or volume. Where the initial 3D image 514 is registered to the additional 3D image, a registered initial 3D image is formed. In each of these cases, the set of additional projection images 522 can be recombined with the registered initial projection images 538, or the registered initial 3D image/volume can be recombined with the additional 3D image/volume to form the enhanced 3D image/volume 528.

Figure 6:
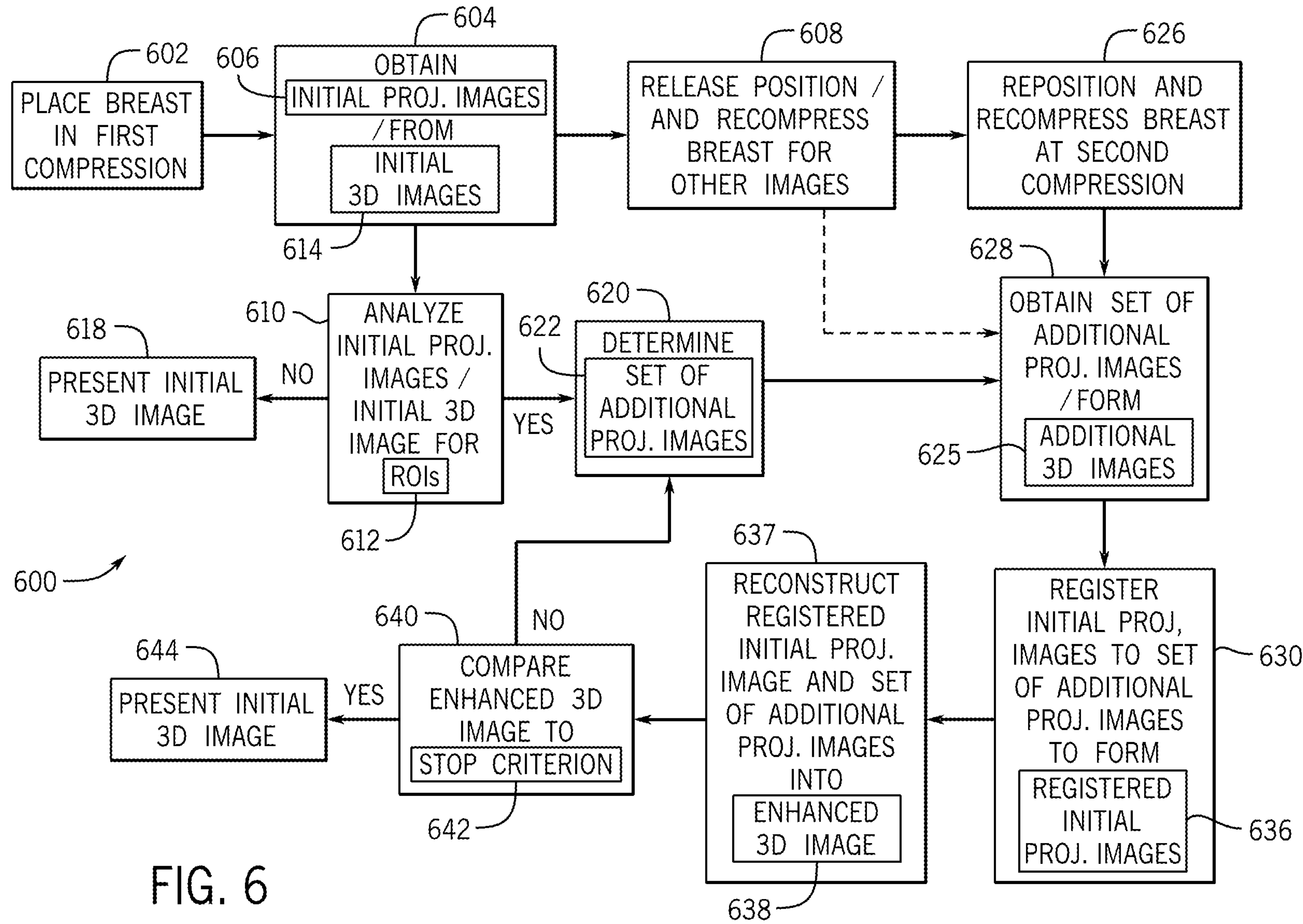
FIG. 6 is a flowchart illustrating the operation of the mammography system in an alternative embodiment of FIG. 5 in accordance with the disclosure.

In one particular exemplary embodiment of this method 500, a method 600 shown in FIG. 6 includes an initial step 602 where the breast 64 is positioned between the compression paddle 40 and the detector 18 in a first compression/position to acquire a set of initial projection images 606 of the breast 64 in a DBT imaging procedure. The position of the breast 64 for the set of initial projection images 606 can be for either a CC view or an MLO view. Once compressed, in step 604, the x-ray system 10 is operated in a DBT imaging procedure to obtain the set of initial projection images 606 of the breast 64 to be analyzed by the user and/or controller 44/CAD system, optionally after reconstruction into an initial 3D image 614, to determine the presence of any ROI(s) 612 within the set of initial projection images 606 and/or initial 3D image 614. Subsequently, in step 608 the breast 64 is released, where the imaging procedure has been completed, and optionally repositioned and recompressed on the x-ray system 10 to perform another DBT imaging procedure to acquire other images of different views of the breast 64, such as the other of the CC/MLO view from that of the set of initial projection images 606. Concurrently with the decompression, repositioning and recompression of the breast 64 on the x-ray system 10 in step 608, in step 610 the set of initial projection images 606 are analyzed and/or reconstructed into an initial 3D image 614 that is analyzed by the user and/or CAD/controller 44 to determine the presence of any ROI(s) 612 within the set of initial projection images 606/initial 3D image 614.

If no ROIs 612 are located in the set of initial projection images 606/initial 3D image 614, the method 600 proceeds to step 618 to present the finding of no ROIs 612 and continues to obtain other projection images and/or terminates the imaging procedure.

Alternatively, if one or more ROI(s) 612 are found in the set of initial projection images 606/initial 3D image 614, in step 620 the controller 44 utilizes the information from the set of initial projection images 606/initial 3D image 614 regarding the location and/or type of ROI(s) 612 present in the manner described previously to determine a set of additional projection images 622 to be acquired by the x-ray system 10 in a DBT imaging procedure in order to obtain further diagnostic information concerning the ROI(s) 612. To obtain the set of additional projection images 622, in step 626 the breast 64 is recompressed on the x-ray system 10 at a different compression than the first compression employed for the set of initial projection images 606, i.e., at a second compression, which can alternatively be done in step 608 if no intervening images are obtained. The second compression is any position and compression of the breast 64 on the x-ray system 10 used to obtain the set of additional projection images 622 of the breast 64 after releasing the breast 64 from the position and compression used to acquire the set of initial projection images 606, as the position and compression employed to obtain the set of additional projection images 622 will not be identical to that used for the set of initial projection images 606, i.e., the first compression. Once positioned on the x-ray system 10 at the second compression, in step 628 the x-ray system 10 is operated in a DBT imaging procedure to obtain the set of additional projection images 622 of the breast 64.

Subsequently, in step 630 the set of initial projection images 606 obtained at the first compression and the set of additional projection images 622 obtained at the second compression are registered with one another, as each are obtained using similar views (both in CC or in MLO) of the breast 64. Alternatively, the registration can be performed between the initial 3D image/volume 614 formed from the set of initial projection images 606 and an additional 3D image/volume 625 reconstructed from the set of additional projection images 622. The algorithm utilized for the registration of the set of initial projection images 606 to the set of additional projection images 622, or the 3D volumes reconstructed therefrom, respectively, is any suitable registration algorithm, such as that disclosed in Clément Jailin et al 2023 *Biomed. Phys. Eng. Express* 9 035003, the entirety of which is expressly incorporated by reference herein for all purposes, and can be included as a part of the controller 44 or as a set of executable instructions stored on the workstation and accessible by the controller 44 in order to perform the registration step 630. As step 630, in one embodiment, registers the set of initial projection images 606 to the set of additional projection images 622, or initial 3D image/volume 614 to additional 3D image/volume 625, or any combination thereof, where the output of the registration in step 630 is a set of registered initial projection images 634.

Concurrently with or subsequent to the registration in step 630, in step 637 the set of registered initial projection images 634 and the set of additional projection images 622, and optionally initial HE 3D image 625, are recombined or reconstructed into an enhanced 3D image 638 including information regarding the location and other characteristics of the ROI(s) 612 therein.

In step 640, the enhanced 3D image 638 is compared with the stop criterion/criteria 642 in manner described previously. If the enhanced 3D image 638 meets or exceeds the selected stop criterion/criteria 642, the method 600 proceeds to step 644 to present the enhanced 3D image 638 and visualization of the ROI(s) 612 therein for review by the user and/or physician and can terminate the screening imaging procedure.

Alternatively, should the enhanced 3D image 638 not meet the required stop criterion 642 as determined in step 640, the method returns to step 620 where the controller 44 utilizes the information from the enhanced 3D image 638 on the location and/or type of ROI(s) 612 present to imaging parameters for a further set of additional projection images 622 to be acquired by the x-ray system 10 in order to obtain further diagnostic information concerning the ROI(s) 612. The further set of additional imaging parameters for are obtained in step 628 and reconstructed along with the enhanced 3D image 638, to provide a further enhanced 3D image 638 for comparison with the stop criterion 642 in step 640. The method 600 can proceed in this iterative manner until the result in step 640 is that the enhanced 3D image 638 meets or exceeds the stop criterion 642, wherein the method 600 proceeds to step 644 to present the enhanced 3D image 638 and visualization of the ROI(s) 612 therein for review by the user and/or physician and terminates the screening imaging procedure.

Figure 7:
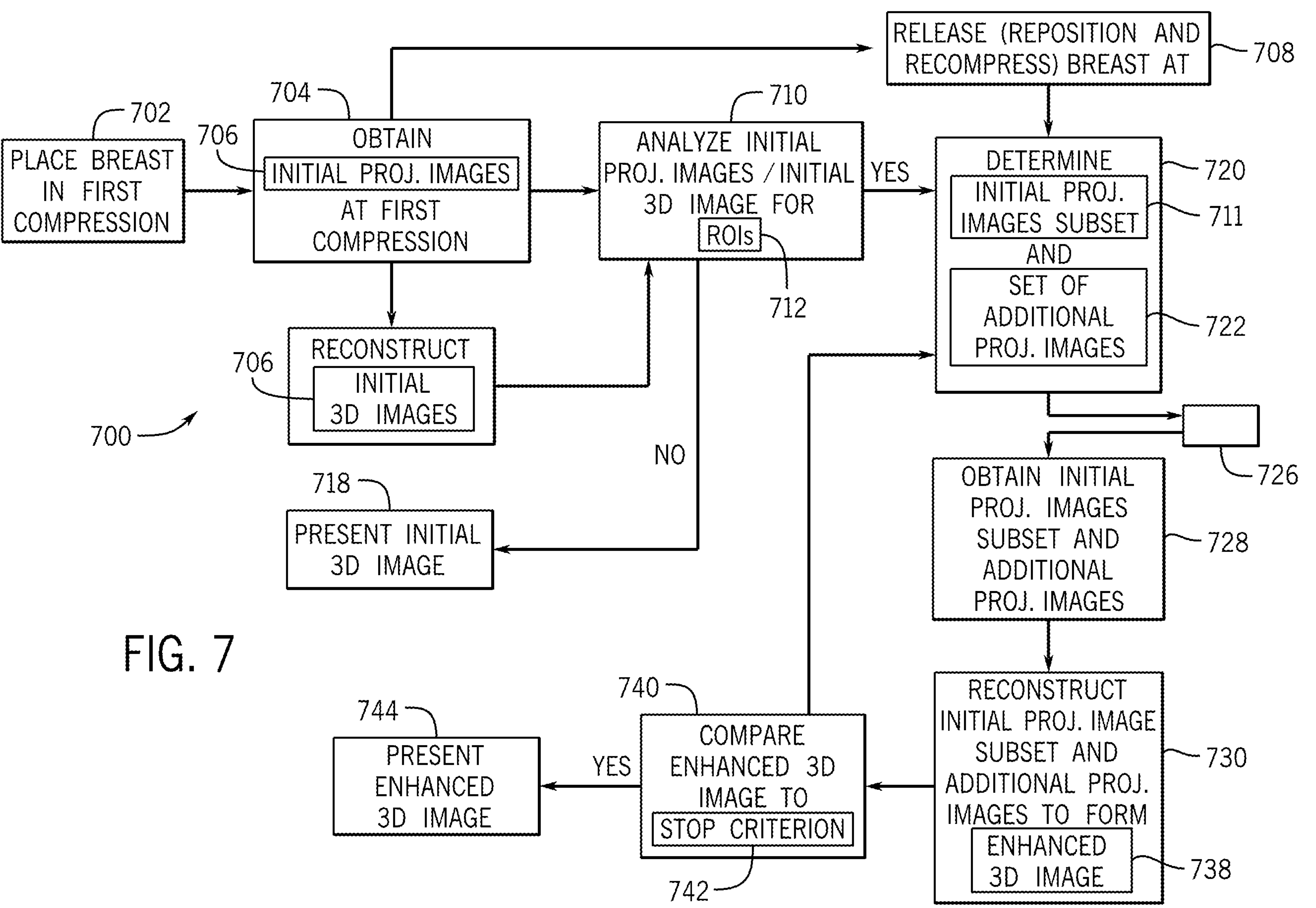
FIG. 7 is a flowchart illustrating the operation of the mammography system in accordance with a fourth embodiment of the disclosure.

In a fourth exemplary embodiment, and optionally in association with any other embodiment described herein, with reference to FIG. 7 the method 700 includes an initial step 702 where the breast 64 is positioned between the compression paddle 40 and the detector 18 in a first compression/position to acquire a set of initial projection images 706 of the breast 64 in a DBT imaging procedure. The position of the breast 64 for the set of initial projection images 706 can be for either a CC view or an MLO view. Once compressed, in step 704, the x-ray system 10 is operated in a DBT imaging procedure to obtain the set of initial projection images 706 of the breast 64 to be analyzed by the user and/or controller 44/CAD system, optionally after reconstruction into an initial 3D image 714, to determine the presence of any ROI(s) 712 within the set of initial projection images 706/initial 3D image 714. Subsequently, in step 708 the breast 64 is released, where the imaging procedure has been completed, and optionally repositioned and recompressed on the x-ray system 10 to perform another DBT imaging procedure to acquire other images of different views of the breast 64, such as the other of the CC/MLO view from that of the set of initial projection images 706. Concurrently with the decompression of the breast 64 on the x-ray system 10 in step 708, in step 710 the set of initial projection images 706 are analyzed and/or reconstructed into an initial 3D image 714 that is analyzed by the user and/or CAD/controller 44 to determine the presence of any ROI(s) 712 within the set of initial projection images 706/initial 3D image 714.

If no ROIs 712 are located in the set of initial projection images 706/initial 3D image 714, the method 700 proceeds to step 718 to present the finding of no ROIs 712 and continues to obtain other images and/or terminates the imaging procedure.

Alternatively, if one or more ROI(s) 712 are found in the set of initial projection images 706/initial 3D image 714, in step 720 the controller 44 utilizes the information from the set of initial projection images 706/initial 3D image 714 regarding the location and/or type of ROI(s) 712 present in the manner described previously to determine both a subset 711 of the set of initial projection images 706 to re-acquire and a set of additional projection images 722 to be acquired by the x-ray system 10 in subsequent DBT imaging procedures in order to obtain further diagnostic information concerning the ROI(s) 712. The initial projection image subset 711 can be selected automatically or manually from the set of initial projection images 706 as reprojections of the individual images in the set of initial projection images 706 that optimally show the ROI(s) 712 detected in the set of initial projections 706.

To obtain the initial projection image subset 711 and the set of additional projection images 722, in step 726 the breast 64 is recompressed on the x-ray system 10 at a different compression than the first compression employed for the set of initial projection images 706, i.e., at a second compression, which could also be performed in step 708 if no other images are being obtained. Once positioned on the x-ray system 10 at the second compression to obtain images of the breast 64 at the same view for the initial projection images 706, in step 728 the x-ray system 10 is operated in a first DBT imaging procedure to obtain the initial projection image subset 711 and in a second DBT imaging procedure to obtain set of additional projection images 722/of the breast 64.

In step 730, as they are obtained at the same compression of the breast 64, i.e., the second compression, the initial projection image subset 711 and the set of additional projection images 722 are recombined or reconstructed into an enhanced 3D image 738 including information regarding the location and other characteristics of the ROI(s) 712 therein.

In step 740, the enhanced 3D image 738 is compared with the stop criterion/criteria 742 in manner described previously. If the enhanced 3D image 738 meets or exceeds the selected stop criterion/criteria 742, the method 700 proceeds to step 744 to present the enhanced 3D image 738 and visualization of the ROI(s) 712 therein for review by the user and/or physician and can terminate the screening imaging procedure.

Alternatively, should the enhanced 3D image 738 not meet the required stop criterion 742 as determined in step 740, the method returns to step 720 where the controller 44 utilizes the information from the enhanced 3D image 738 on the location and/or type of ROI(s) 712 present to determine imaging parameters for a further set of additional projection images 722 to be acquired by the x-ray system 10 in order to obtain further diagnostic information concerning the ROI(s) 712. The further set of additional projection images 722 are obtained in step 728 and reconstructed along with the enhanced 3D image 738 to provide a further enhanced 3D image 738 for comparison with the stop criterion 742 in step 740. The method 700 can proceed in this iterative manner until the result in step 740 is that the enhanced 3D image 738 meets or exceeds the stop criterion 742, wherein the method 700 proceeds to step 744 to present the enhanced 3D image 738 and visualization of the ROI(s) 712 therein for review by the user and/or physician and terminates the screening imaging procedure.

With regard to any of the previously described embodiments of the disclosure, in a fifth exemplary embodiment of the disclosure, after the controller 44/CAD system has determined the presence of one or more ROIs in the initial projection images and/or initial 3D image, at the end of the step 311,420,520,620,720 where the imaging parameters (tube position(s), energy level, number of acquisition, etc.) for the set of additional projection images has been determined, the controller 44 can automatically move the radiation source 16 into the proper location for beginning the procedure for obtaining the set of additional projection images. This movement can be accompanied by an indication to the user of the x-ray system 10 that ROIs have been detected and that the set of additional projection images is required.

Figure 8:
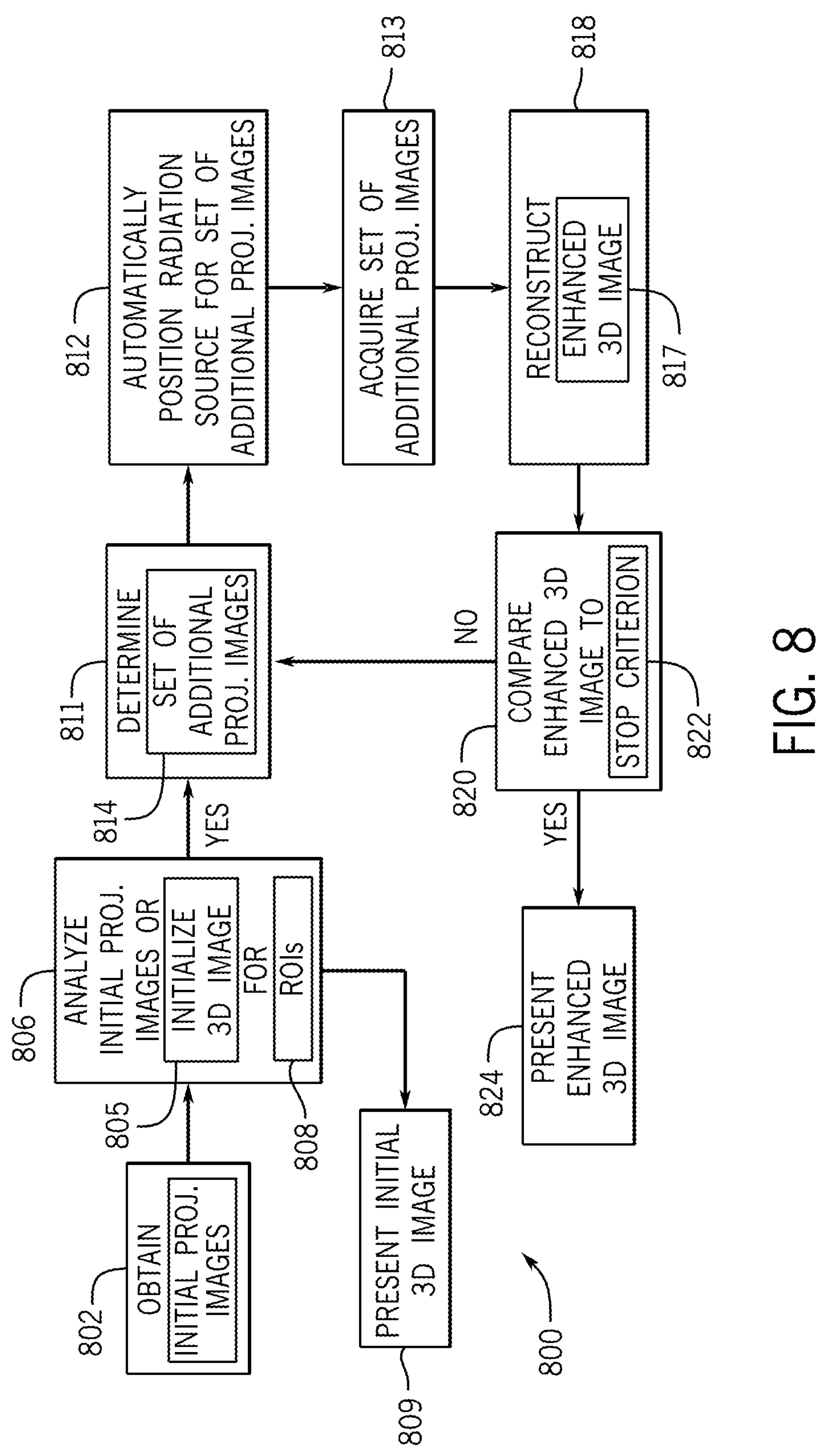
FIG. 8 is a flowchart illustrating the operation of the mammography system in accordance with a fifth embodiment of the disclosure.

According to an exemplary embodiment of this method, and optionally in association with any other embodiment described herein, with reference to FIG. 8, in the method 800 after compression of the breast on the x-ray system 10 between the detector 18 and the compression paddle 40, in step 802 the initial projection images 804 are obtained of the breast 64 at various angular positions of the radiation source 16 relative to the compressed breast 64 and the radiation detector 18. In step 806, the initial projection images 804, and/or an initial 3D image 805 that is reconstructed from the initial projection images 804, is analyzed to determine the presence of any suspicious areas or regions of interest (ROIs) 808 within the initial projection images 804/initial 3D image 805.

If no ROI(s) 808 are located in the initial projection images 804 or initial 3D image 805, in step 809 the initial 3D image 805 is presented on the display 50 along with the finding of no ROI(s) 808. However, should the user or controller 44 determine a ROI 808 is present in the initial projection images 804/initial 3D image 805, in step 811 the controller 44 utilizes information from the initial projection images 804/initial 3D image 805 on the location and/or type of ROI(s) 808 present within the breast 64 to determine imaging parameters, in the manner described previously, for a set of additional projection images 814 to be acquired by the x-ray system 10 in order to obtain further diagnostic information concerning the ROI(s) 808.

Once the imaging parameters for the set of additional projection images 814 are determined, in step 812 the x-ray system 10 automatically moves the gantry 15 and the radiation source 16 to a position relative to the breast 64 where the initial image of the set of additional projection images 814 is to be obtained. The movement of the gantry 15 and radiation source 16 can be accompanied by an indication (not shown) of the number and type of images forming the set of additional projection images 814 that are to be obtained, optionally along with information regarding the number and type of ROI(s) 808 necessitating the set of additional projection images 814.

In the method 800, either automatically or upon acknowledgement by the user, e.g., via the workstation 43, the set of additional projection images 814 are obtained in step 813 with the breast 64 under the same compression as employed for the acquisition of the initial projection images 804 in step 802, such that the initial projection images 804 and set of additional projection images 814 are acquired with the breast 64 in the same position.

After acquisition of the set of additional projection images 814, in step 818 the controller 44 processes each of the initial projection images 804, and/or the initial 3D image 805, along with each of the set of additional projection images 814 to form or reconstruct one or more enhanced images, e.g., an enhanced 3D image 817 clearly presenting the location and other characteristics of the ROI(s) 308 within the enhanced 3D image 817 for diagnostic review by the user and/or reviewing physician.

In subsequent step 820, the enhanced 3D image 817 is analyzed by the controller 44 to determine whether the enhanced 3D image 817 meets or exceeds a stop criterion/criteria 822 for the imaging procedure. If in step 820, the enhanced 3D image 817 meets or exceeds the selected stop criterion/criteria 822, the method 800 proceeds to step 824 to present the enhanced 3D image 817 and visualization of the ROI(s) 808 therein for review by the user and/or physician and terminates the screening imaging procedure.

Alternatively, should the enhanced 3D image 817 not meet the required stop criterion/criteria 822 as determined in step 820, the method returns to step 811 where the controller 44 utilizes the information from the enhanced 3D image 817 on the location and/or type of ROI(s) 808 present to determine a further set of additional projection images 814 to be performed by the x-ray system 10 in order to obtain further diagnostic information concerning the ROI(s) 808. The further set of additional projection images 814 are obtained in step 812 and reconstructed along with the enhanced 3D image 817 to provide a further enhanced 3D image 817 for comparison with the stop criterion 822 in step 820. The method 800 can proceed in this iterative manner until the result in step 820 is that the enhanced 3D image 817 meets or exceeds the stop criterion 822, where the method 800 proceeds to step 824 to present the enhanced 3D image 817 and visualization of the ROI(s) 808 therein for review by the user and/or physician and terminates the screening imaging procedure.

Figure 9:
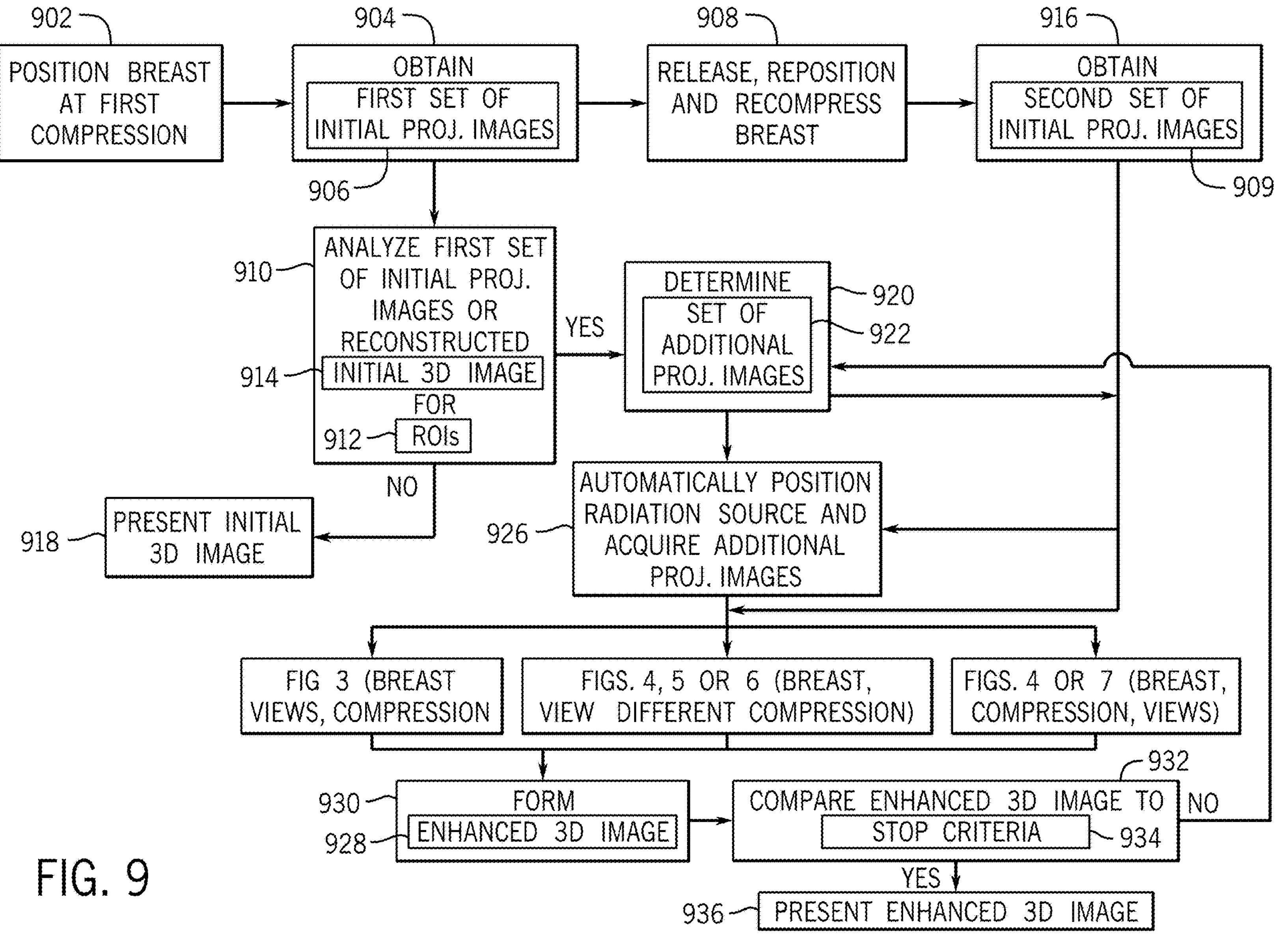
FIG. 9 is a flowchart illustrating the operation of the mammography system in an alternative embodiment of FIG. 8 in accordance with the disclosure.

In an alternative embodiment to the method 800, and optionally in association with any other embodiment described herein, as shown in the exemplary illustrated embodiment of FIG. 9, the method 900 is similar to method 800 but includes obtaining the initial projection images 904 at the first compression and obtaining the set of additional projection images 914 at a second compression. More specifically, the method 900 involves the positioning of the breast 64 in step 902 between the compression paddle 40 and the detector 18 at a first compression, which can be either cranial-caudal (CC) images or mediolateral oblique (MLO) images of the breast 64. Once compressed, in step 904, the x-ray system 10 is operated in a DBT imaging procedure to obtain the first set of initial projection images 906 of the breast 64 at selected angular positions of the radiation source 16 relative to the radiation detector 18 and the breast 64. Subsequently, in an optional step 908, the breast 64 is released, repositioned and recompressed in order to operate the x-ray system 10 in another DBT imaging procedure in subsequent optional step 916 to obtain a second set of initial projection images 909 in the other of the CC/MLO view from that of the first set of initial projection images 906. Alternatively, the second set of initial projection images 909 can be CC and/or MLO images of the other breast 64. Concurrently with the decompression, repositioning and second compression of the breast 64 on the x-ray system 10 in step 908 for the subsequent acquisition, or when steps 908 and 916 are omitted, in step 910 the first set of initial projection images 906 is analyzed or reconstructed into an initial 3D image 914 that is analyzed by the user and/or CAD/controller 44 to determine the presence of any ROI(s) 912 within the initial projection images 906 or initial 3D image 914. Further, during and/or subsequent to the analysis of the initial 3D image 914, in step 916, the x-ray system 10 is operated to perform the subsequent acquisition of the second set of LE images 909 of the breast 64.

If no ROIs 912 are located in the initial 3D image 914, the method 900 proceeds to step 918 to present the finding of no ROIs 912 within the initial 3D image 914 and terminates the screening imaging procedure. Alternatively, if one or more ROI(s) 912 are found in the initial 3D image 914, in step 920 the controller 44 utilizes the information from the first set of initial projection images 906 and/or the initial 3D image 914 regarding the location and/or type of ROI(s) 912 present in the manners described previously to determine imaging parameters for a set of additional projection images 922 to be obtained by the x-ray system 10 in a DBT imaging procedure in order to obtain further diagnostic information concerning the ROI(s) 912. In step 926, the imaging parameters can be used to position the radiation source 16 to acquire the set of additional projection images 922 in an automatic or manually directed manner.

In one exemplary embodiment for the application of the imaging parameters and acquiring the set of additional projection images 922 in step 926, if the second set of initial projection images 909 is acquired in step 908 and is of a different view of the same breast 64, the imaging parameters for the set of additional projection images 922 to be obtained can be for the breast 64 at the same compression employed for obtaining the second set of initial projection images 909. Thus, the controller 44 can automatically position the gantry 15 and radiation source 16 to obtain the initial image of the set of additional projection images 922 after the second set of initial projection images 909 is obtained, and provide an indication (not shown) of the number and type of images forming the set of additional projection images 922 that are to be obtained, as described previously. Further, either automatically or upon acknowledgement by the user, e.g., via the workstation 43, the set of additional projection images 922 are obtained in step 926, and the enhanced 3D image 928 is iteratively constructed in the manner(s) of FIG. 3 described previously regarding the initial projection images 909 and set of additional projection images 922 obtained of the breast at the same compression by comparison in step 932 with the stop criteria 934 to provide the enhanced 3D image 928 for presentation and diagnostic review in step 936.

Alternatively, in another for the application of the imaging parameters and acquiring the set of additional projection images 922 in step 926, if the second set of initial projection images 909 are obtained on a breast 64 different than for the first set of initial projection images 906, or if the breast 64 is simply decompressed and released without obtaining the second set of initial projection images 909 in step 916, the imaging parameters determined in step 920 for the set of additional projection images 922 to be obtained can be for the breast 64 on which the first set of initial projection images 906 was obtained, but at a different compression. In this embodiment, the breast 64 is positioned at a second compression on the x-ray system 10 to obtain the set of additional projection images 922 at a view(s) similar to that employed for the first set of initial projection images 904. The controller 44 automatically positions the gantry 15 and radiation source 16 to obtain the initial image of the set of additional projection images 922 and can provide an indication (not shown) of the number and type of images forming the set of additional acquisitions 922/HE images 924 that are to be obtained, as described previously. Further, either automatically or upon acknowledgement by the user, e.g., via the workstation 43, the set of additional projection images 922 are obtained, such that the first set of initial projection images 904 and set of additional projection images 922 can be subsequently, and optionally, registered and iteratively reconstructed to form the enhanced 3D image 928 in the manner(s) of FIGS. 4, 5 and 6 described previously regarding the initial projection images and set of additional projection images obtained of the breast 64 at different compressions by comparison in step 932 with the stop criteria 934 to provide the enhanced 3D image 928 for presentation and diagnostic review in step 936.

Further, in still another for the application of the imaging parameters and acquiring the set of additional projection images 922 in step 926, if the second set of initial projection images 909 are obtained on a breast 64 different than for the first set of initial projection images 906, or if the breast 64 is simply decompressed and released without obtaining the second set of initial projection images 909 in step 916, the imaging parameters for the set of additional projection images 922 to be obtained can include imaging parameters for the additional projection images 922 and a subset of the first set of LE images 906, but to be obtained/reprojected at a different or second compression of the breast 64. In this embodiment, the breast 64 is positioned at a second compression on the x-ray system 10 to obtain both a subset of the first set of initial projection images 906 and the set of additional acquisitions 922/HE images 924. The controller 44 automatically positions the gantry 15 and radiation source 16 to obtain the initial image of the subset of the first set of initial projection images 904, and can provide an indication (not shown) of the number and type of images forming the subset of the first set of initial projection images 904 and the set of additional projection image 922 that are to be obtained, as described previously. Further, either automatically or upon acknowledgement by the user, e.g., via the workstation 43, the subset of the first set of initial projection images 904 and the set of additional projection images 922 are obtained, such that the subset of the first set of initial projection images 904 and the set of additional projection images 922 can be subsequently iteratively reconstructed to form the enhanced 3D image 928 in the manner of FIGS. 4 and 7 described previously regarding the initial projection images 904 or subset thereof and set of additional projection images 922 obtained of the breast at the same compression by comparison in step 932 with the stop criteria 934 to provide the enhanced 3D image 928 for presentation and diagnostic review in step 936.

Figure 10:
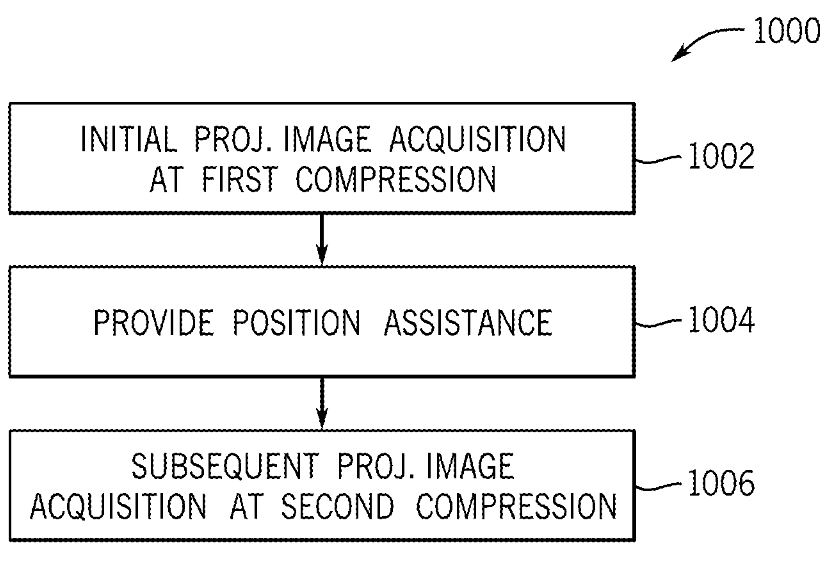
FIG. 10 is a flowchart illustrating the operation of the mammography system including a positioning assistance indicator in accordance with the disclosure.
Figure 11:
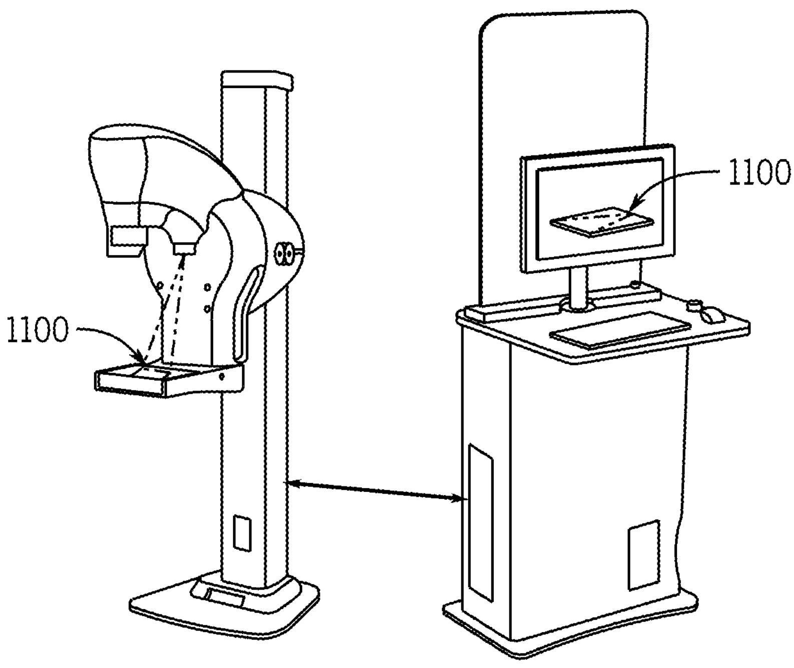
FIG. 11 is a schematic view of the positioning assistance indicator of FIG. 10 on the mammography system in accordance with the disclosure.

Referring now to FIGS. 10 and 11, in still a further exemplary embodiment of the invention, as an addition to any of the prior described methods 300-900, as illustrated in exemplary method 1000 between the step 1002 of acquiring the first set of initial projection images at the first compression on the x-ray system 10 and the step 1004 of obtaining the second set of initial projection images, the subset of the first set of initial projection images and/or the additional projection images at the second compression on the x-ray system 10, the methods 300-900 can include a position assistance step 1006. In this step 1006, which can be automatically employed by the x-ray system 10 or selectively employed by the user through the user interface 56 of the x-ray system 10, the x-ray system 10 provides an indication 1100 (FIG. 10) to the user regarding the compressed position of the breast 64 during the acquisition of the first initial projection images for use a guide for the positioning of the breast 64 for the acquisition of the subsequent projection images. The indication 1100 can take any suitable form, such as representation of the breast 64 position from the first initial projection image acquisition superimposed on a camera image of the breast 64 being positioned for the acquisition of the subsequent projection images present on the display 56, or a visible outline or similar shape of the breast 64 position from the first initial image acquisition projected onto the detector 18 and the breast 64 being positioned for the acquisition of the subsequent projection images. The position of the indication 1100 relative to the actual location of the breast 64 being positioned for the acquisition of the subsequent projection images enables the user to closely approximate the positions of the breast 64 in each of the first initial projection image and subsequent projection image acquisitions, thereby enhancing the quality of the registration and/or recombination of the various projection images to form the reconstructed enhanced 3D images for diagnostic purposes.

In any of the aforementioned and described embodiments, the initial projection images utilized for the ROI analysis by the CAD system/controller 44 can be either one or more CC projection images, or one or more MLO projection images obtained in a DBT imaging procedure, and the one or more additional projection images can be either one or more CC projection images, or one or more MLO projection images obtained in a DBT imaging procedure.

Finally, it is also to be understood that the system 10 may include the necessary electronics, software, memory, storage, databases, firmware, logic/state machines, microprocessors, communication links, displays or other visual or audio user interfaces, printing devices, and any other input/output interfaces to perform the functions described herein and/or to achieve the results described herein. For example, as previously mentioned, the system may include at least one processor and system memory/data storage structures, which may include random access memory (RAM) and read-only memory (ROM). The at least one processor of the system 10 may include one or more conventional microprocessors and one or more supplementary co-processors such as math co-processors or the like. The data storage structures discussed herein may include an appropriate combination of magnetic, optical and/or semiconductor memory, and may include, for example, RAM, ROM, flash drive, an optical disc such as a compact disc and/or a hard disk or drive.

Additionally, a software application that adapts the controller to perform the methods disclosed herein may be read into a main memory of the at least one processor from a computer-readable medium. The term "computer-readable medium", as used herein, refers to any medium that provides or participates in providing instructions to the at least one processor of the system 10 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

While in embodiments, the execution of sequences of instructions in the software application causes at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software.

It is understood that the aforementioned compositions, apparatuses and methods of this disclosure are not limited to the particular embodiments and methodology, as these may vary. It is also understood that the terminology used herein is for the purpose of describing particular exemplary embodiments only, and is not intended to limit the scope of the present disclosure which will be limited only by the appended claims.

We claim:

1. A method for determining the need for generation of enhanced diagnostic images of a patient, the method comprising the steps of:

a. providing an imaging system comprising:
i. a radiation source operable at to emit radiation,
ii. a detector alignable with the radiation source, the detector having a surface on which an object to be imaged is adapted to be positioned; and
iii. a controller operably connected to the radiation source and the detector to control the operation of the radiation source and detector to generate image data in an imaging procedure performed by the imaging system, the controller including a central processing unit and interconnected database for processing the image data from the detector to create images,
iv. a display operably connected to the controller for presenting information to a user; and
v. a user interface operably connected to the controller to enable user input to the controller,
b. positioning the object on the surface between the radiation source and the detector;
c. acquiring one or more initial projection images of the object;
d. reconstructing an initial 3D image of the object from the one or more initial projection images;
e. analyzing the initial projection images or the initial 3D image to locate one or more triggering attributes, characteristics or findings within the object;
f. determining one or more imaging parameters for a set of one or more additional projection images of the object, the set of additional projection images to be acquired at one or more x-ray tube positions different than employed for acquiring the one or more initial projection images if one or more triggering attributes, characteristics or findings are located in the object;
g. acquiring the set of additional projection images;
h. processing the initial 3D image and the set of additional projection images to form an enhanced 3D image; and
i. comparing the enhanced 3D image to a stop criterion.

2. The method of claim 1, further comprising the steps of:
a. determining imaging parameters for an additional set of additional projection images of the object if the enhanced 3D image does not meet the stop criterion, the additional set of additional projection images acquired at one or more x-ray tube positions different than employed for acquiring the one or more initial projection images if one or more triggering attributes, characteristics or findings are located in the object;
b. acquiring the additional set of additional projection images;
c. processing the enhanced 3D image and the additional set of additional projection images to form a further enhanced 3D image; and
d. comparing the further enhanced 3D image to the stop criterion.

3. The method of claim 1, wherein the step of acquiring the set of additional projection images of the object comprises acquiring one or more single energy or dual energy images of the object.

4. The method of claim 3, wherein the step of processing the initial 3D image and the set of additional projection images to form the enhanced 3D image comprises processing the initial 3D image and the one or more additional projection images to form the enhanced 3D image.

5. The method of claim 1, wherein the imaging system is a mammography imaging system including a gantry supporting the radiation source and the detector and operably connected to the controller, a compression plate disposed on the gantry and movable with respect to the radiation source and the detector, wherein the object is a breast, and wherein the step of positioning the object on the surface between the radiation source and the detector comprises the steps of:
a. placing the breast on the surface of the detector; and
b. moving the compression plate to compress the breast at a first compression between the compression plate and the surface.

6. The method of claim 5, further comprising the steps of:
a. moving the compression plate to decompress the breast from the first compression between the compression plate and the surface after acquiring the one or more initial projection images of the breast; and
b. moving the compression plate to recompress the breast at a second compression between the compression plate and the surface after analyzing the initial 3D image.

7. The method of claim 6, wherein the step of acquiring one or more initial projection images of the breast comprises acquiring one or more initial projection images of the breast in a cranial-caudal (CC) or mediolateral oblique (MLO) view at the first compression, and wherein the step of acquiring the set of additional projection images comprises acquiring the set of additional projection images in a CC or MLO view at the second compression after moving the compression plate to recompress the breast at the second compression.

8. The method of claim 7, wherein the one or more initial projection images obtained at the first compression and the set of additional projection images obtained at the second compression are acquired in the same CC or MLO view, and wherein the method further comprises the steps of:
a. registering the one or more initial projection images to the set of additional projection images to form one or more registered initial projection images after acquiring the set of additional projection images; and
b. reconstructing the registered initial projection images into the initial 3D image prior to processing the initial 3D image and the set of additional projection images to form the enhanced 3D image.

9. The method of claim 8, wherein the step of registering the one or more initial projection images to the set of additional projection images to form one or more registered initial projection images comprises the steps of:
a. reconstructing the one or more initial projection images into an initial 3D image;
b. reconstructing the set of additional projection images into an additional 3D image;
c. registering the initial 3D image to the additional 3D image to form a registered initial 3D image; and
d. combining the registered initial 3D image and the additional 3D image to obtain the 3D enhanced image.

10. The method of claim 7, wherein the step of acquiring one or more initial projection images of the breast comprises acquiring a first set of initial projection images at the first compression, and wherein the step of acquiring the set of additional projection images comprises:
a. acquiring a second set of initial projection images at the second compression; and
b. acquiring the set of additional projection images at the second compression.

11. The method of claim 10, wherein the step of acquiring the second set of initial projection images comprises:
a. determining a subset of the first set of initial projection images containing information on one or more triggering attributes, characteristics or findings located within the breast; and
b. acquiring reprojections of the subset of the first set of initial projection images at the second compression to form the second set of initial projection images.

12. The method of claim 1, wherein the step of determining the one or more imaging parameters for a set of one or more additional projection images of the object comprises manually determining the one or more imaging parameters, automatically determining the one or more imaging parameters employing fixed parameters based on types, positions and numbers of one or more triggering attributes, characteristics or findings located in the object, automatically determining the one or more imaging parameters based on an artificial intelligence for optimizing images on one or more triggering attributes, characteristics or findings located in the object, and combinations thereof.

13. The method of claim 1, further comprising the step of automatically adjusting a position of the radiation source relative to the detector based upon the determined imaging parameters for the set of one or more additional projection images prior to acquiring the set of one or more additional projection images.

14. The method of claim 1, wherein the stop criterion is selected from the group consisting of an image quality score, a confidence score, variations in one or more determined characteristics of the object, and combinations thereof.

15. The method of claim 1, wherein the step of analyzing the initial 3D image is performed manually through the user interface.

16. The method of claim 1, wherein the imaging system includes a collimator mounted to the radiation source, and wherein the step of acquiring the one or more additional projection images of the object comprises the steps of:

a. adjusting the collimator on the radiation source; and b. acquiring the set of one or more additional projection images.

17. The method of claim 1, wherein the imaging system includes a computer aided detection (CAD) system operably connected to the controller and configured to analyze images created by the controller and locate one or more triggering attributes, characteristics or findings within the object, and wherein the step of analyzing the initial 3D image to locate one or more triggering attributes, characteristics or findings within the object comprises automatically detecting ROIs within the object with the CAD system.

18. A mammography system comprising:

a. a radiation source operable at to emit radiation at multiple energy levels, a detector alignable with the radiation source, the detector having a surface on which an object to be imaged is adapted to be positioned; and b. a controller operably connected to the radiation source and the detector to control the operation of the radiation source and detector to generate image data in an imaging procedure performed by the imaging system, the controller including a central processing unit and interconnected database for processing the image data from the detector to create images, c. a display operably connected to the controller for presenting information to a user; and d. a user interface operably connected to the controller to enable user input to the controller, wherein the controller is configured to acquire one or more initial projection images of the object, to reconstruct an initial 3D image of the object from the one or more initial projection images, to analyze the initial 3D image to locate one or more triggering attributes, characteristics or findings within the object, to determine one or more imaging parameters for a set of one or more additional projection images of the object, the set of one or more additional projection images to be acquired with one or more radiation source positions different than employed for acquiring the one or more initial projection images if one or more triggering attributes, characteristics or findings are located in the object, to acquire the set of one or more additional projection images, to process the initial 3D image and the set of one or more additional projection images to form an enhanced 3D image, and to compare the enhanced 3D image to a stop criterion.

19. The mammography system of claim 18, wherein the controller is configured to acquire the one or more initial projection images and the set of additional projection images in the same view of the object and to register the one or more initial projection images to the set of additional projection images to form registered initial projection images prior to processing the registered initial projection images and the set of additional projection images to form the enhanced 3D image.

20. The mammography system of claim 17, wherein the controller includes a computer aided detection (CAD) system operably connected to the controller and configured to analyze images created by the controller and locate the one or more triggering attributes, characteristics or findings within the object, and wherein the controller is configured to automatically determine the one or more imaging parameters employing fixed parameters based on types, positions and numbers of triggering attributes, characteristics or findings located in the object, to automatically determine the one or more imaging parameters based on an artificial intelligence for optimizing images of the triggering attributes, characteristics or findings located in the object, and combinations thereof.

21. The mammography system of claim 17, wherein the controller is configured to determine imaging parameters for an additional set of additional projection images of the object if the enhanced 3D image does not meet the image criterion, the additional set of additional projection images acquired with one or more radiation source positions different than employed for acquiring the one or more initial projection images if one or more triggering attributes, characteristics or findings are located in the object, to acquire the additional set of additional projection images, to process the enhanced 3D image and the additional set of additional projection images to form a further enhanced 3D image, and to compare the further enhanced 3D image to the stop criterion.

* * * * *